(12) United States Patent
Hirota et al.

(10) Patent No.: US 6,753,144 B1
(45) Date of Patent: Jun. 22, 2004

(54) BIOCHIP

(75) Inventors: Toshikazu Hirota, Owariasahi (JP); Takao Ohnishi, Nishikasugai-Gun (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/868,832

(22) PCT Filed: Oct. 20, 2000

(86) PCT No.: PCT/JP00/07343

§ 371 (c)(1), (2), (4) Date: Jun. 21, 2001

(87) PCT Pub. No.: WO01/29561

PCT Pub. Date: Apr. 26, 2001

(30) Foreign Application Priority Data

Oct. 22, 1999 (JP) .......................................... 11-301627

(51) Int. Cl.[7] .......................... C12Q 1/68; C12N 11/16; C12M 1/00; C07H 21/04
(52) U.S. Cl. ........................ 435/6; 435/174; 435/283.1; 435/287.2; 422/68.1; 422/100; 536/23.1
(58) Field of Search ..................... 435/6, 287.2, 283.1, 435/174; 422/68.1, 100; 536/23.1

(56) References Cited

U.S. PATENT DOCUMENTS

| | | | | |
|---|---|---|---|---|
| 5,807,522 A | * | 9/1998 | Brown et al. ................. | 422/50 |
| 5,843,662 A | * | 12/1998 | Dean et al. ..................... | 435/6 |
| 6,232,066 B1 | * | 5/2001 | Felder et al. .................. | 435/6 |
| 6,232,072 B1 | * | 5/2001 | Fisher ............................ | 435/6 |
| 6,280,946 B2 | * | 8/2001 | Hyldig-Nielsen et al. ...... | 435/6 |
| 6,458,584 B1 | * | 10/2002 | Mirzabekov et al. .... | 435/287.2 |
| 6,489,159 B1 | * | 12/2002 | Chenchik et al. ......... | 435/287.2 |
| 2002/0015958 A1 | * | 2/2002 | Audeh et al. .................. | 435/6 |

FOREIGN PATENT DOCUMENTS

| | | |
|---|---|---|
| JP | 6-40030 | 2/1994 |
| JP | 8-201265 | 8/1996 |
| WO | 95/11755 | 5/1995 |
| WO | 95/35505 | 12/1995 |

* cited by examiner

Primary Examiner—B J Forman
(74) Attorney, Agent, or Firm—Burr & Brown

(57) ABSTRACT

When genetic analyses are performed using the DNA microarray of the present invention, the inspection accuracy is improved. A sample solution is supplied onto a base plate 10 to prepare the DNA microarray 20 which includes a large number of spots 80 containing capture solutions arranged on the base plate 10. The capture solutions are adapted to specifically react with a specimen and provide information about a structure within the specimen. In the microarray 20, the planar configuration of the spots 80 are substantially circular, and a plurality of spots having different spot sizes are formed on the base plate.

13 Claims, 18 Drawing Sheets

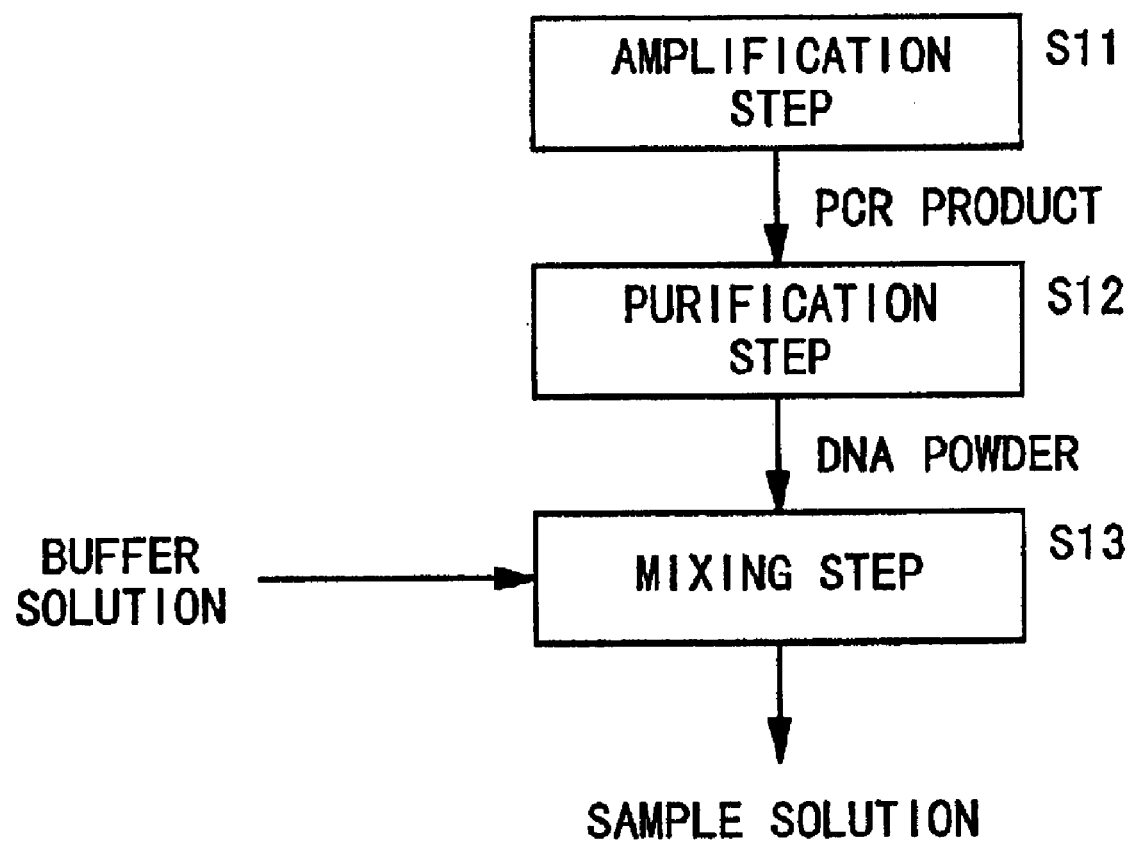

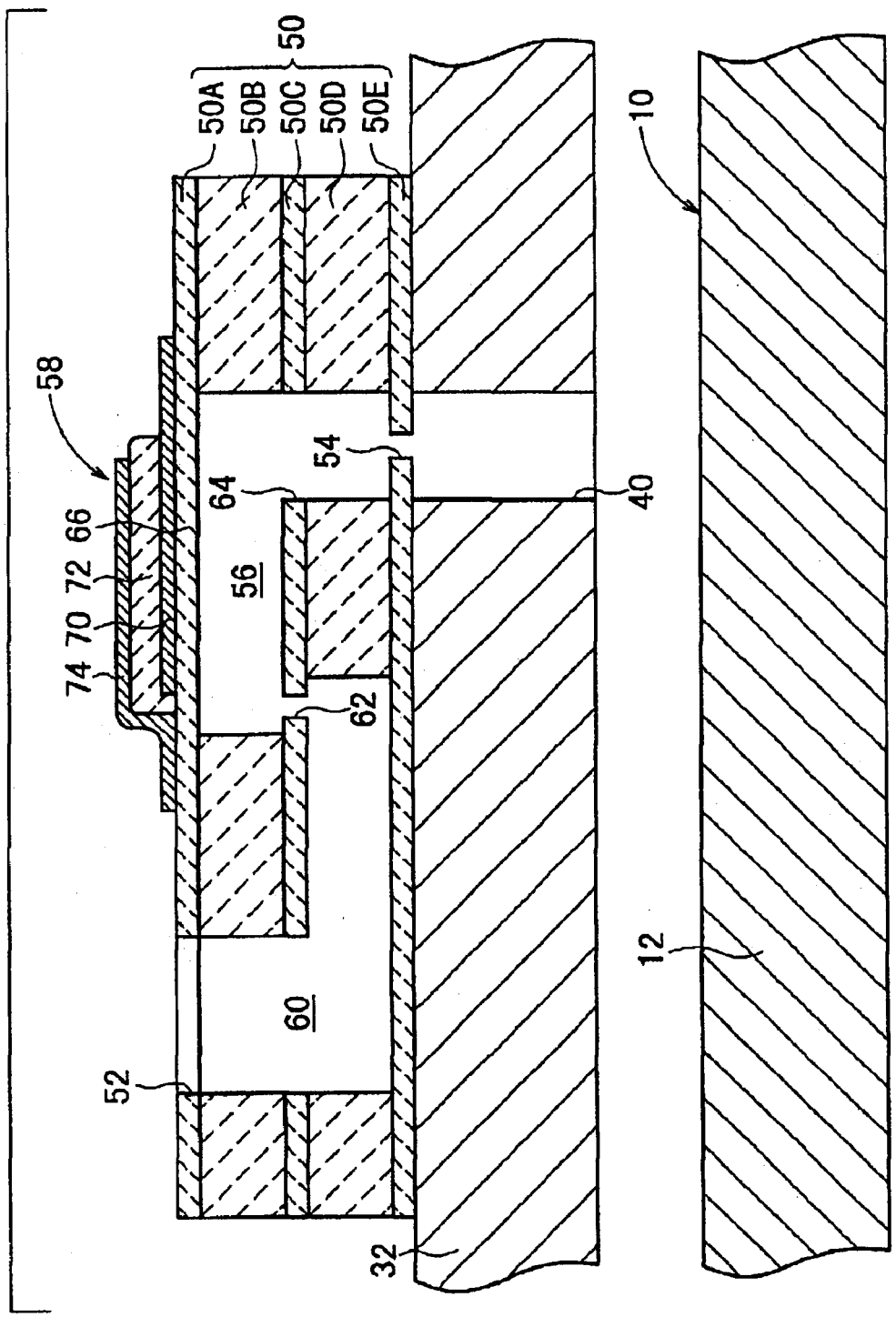

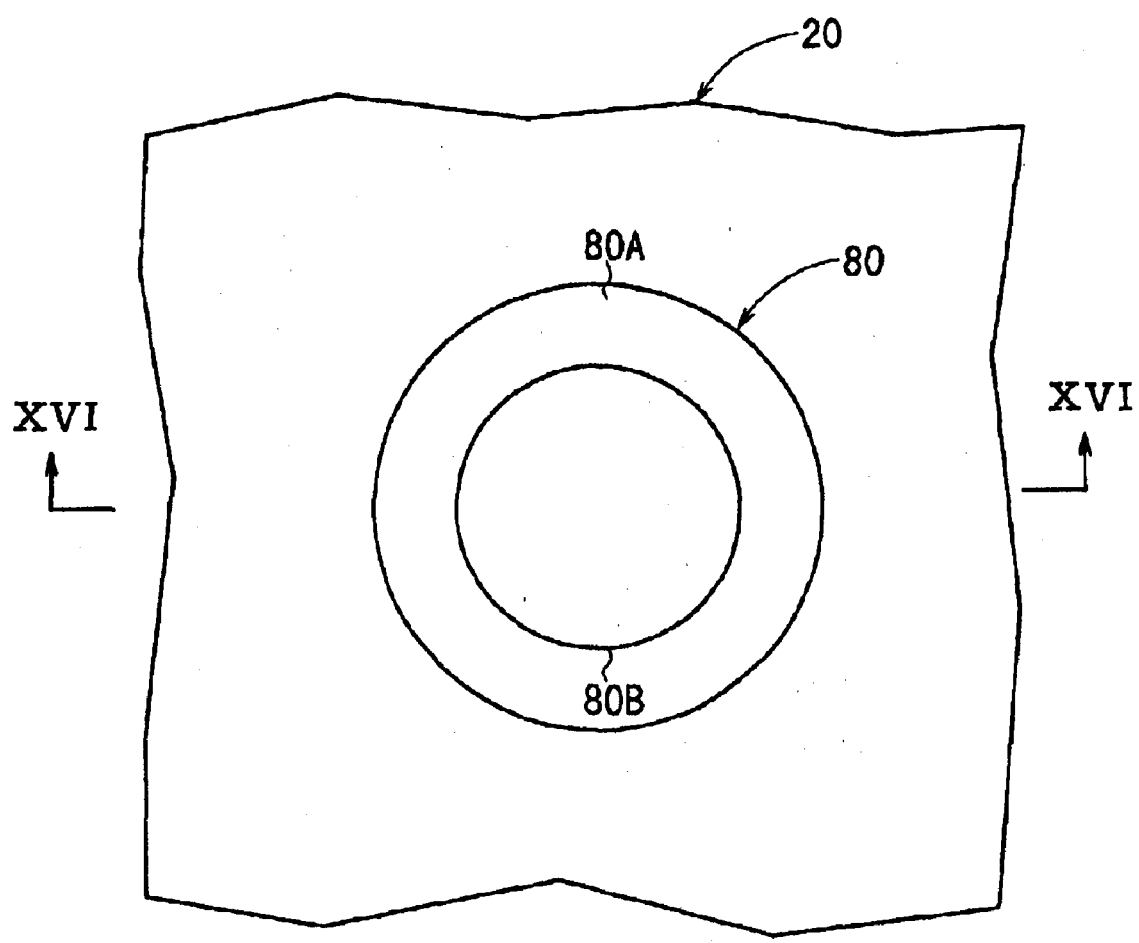

BIOCHIP

FIELD OF THE INVENTION

The present invention relates to a DNA microarray (DNA chip) which specifically reacts with a biochemical specimen and which is used for inspection equipment represented, for example, by a biochip to be used in order to obtain information on a structure of the specimen, especially in which several thousand to not less than ten thousand kinds of different types of DNA fragments are aligned and fixed at a high density as spots on a base plate such as a microscopic glass slide.

BACKGROUND OF THE INVENTION

The method of analyzing the genetic structure has been remarkably progressed in recent years. A large number of genetic structures represented by those of human genes have been clarified. The analysis of the genetic structure uses a DNA microarray (DNA chip) in which several thousand to not less than ten thousand kinds of different types of DNA fragments are aligned and fixed as spots on a base plate such as a microscopic glass slide.

In recent years, there is a demand for enhancing the reproducibility, the quantitative performance in the information obtained from the DNA microarray and obtaining much more information from the DNA microarray. The information obtained from respective spots needs to be correct, uniform, and complex.

Those widely used as the method of forming the spots for the production of the DNA microarray are generally based on a system such as the QUILL system, the pin & ring system, and the spring pin system in which a sample solution containing DNA fragments is supplied (stamped) onto the base plate by using a so-called pin. When any one of the foregoing methods is adopted, it is important to suppress the dispersion of the volume and the shape of each spot so that the distance between the respective spots is maintained to be constant.

On the other hand, in order to realize a higher density, it is also greatly expected to develop a new method which is excellent in productivity and in which the shape control performance for the spot is satisfactory.

The conventional method of forming the spot is based on the supply (stamping) of the sample solution onto the base plate by using the pin. Therefore, the shape of the spot is diversified, for example, due to the shape of the forward end of the pin and/or the residue of the sample solution remaining at the forward end of the pin after the supply. As shown in FIG. 18, spots 200, each of which has many irregularities at the outer circumferential portion, are formed on a base plate 202.

When unknown DNA is inspected by using a DNA microarray arranged with a large number of spots having dispersed shapes, it is apt to be difficult to recognize the fluorescence light emission from the spot with a CCD camera or the like. Therefore, the inspection accuracy may be lowered.

Further, when many irregularities exist at the outer circumferential portion, the sample solution flows through angular portions. Therefore, the sample solutions in the plurality of spots 200 may be mixed with each other.

The present invention has been made taking the foregoing problems into consideration, an object of which is to provide a DNA microarray which makes it possible to improve the inspection accuracy for genetic analyses and which makes it possible to increase the amount of information to be obtained.

Another object of the present invention is to provide a DNA microarray which makes it possible to achieve a high degree of concentration of spots and which makes it possible to perform detailed genetic analyses.

Still another object of the present invention is to provide a DNA microarray which makes it possible to recognize the degree of the reaction with respect to an amount of DNA fragments immobilized in a spot and which makes it possible to obtain an analog inspection result for a specimen, in addition to a digital inspection result to indicate whether or not the reaction occurs.

The applicable range of the present invention is not limited to the DNA microarray in which DNA fragments are aligned and immobilized as spots. The present invention is generally usable for every type of the biochip which specifically reacts with a biochemical specimen and which is used in order to obtain information on the structure of the specimen.

SUMMARY OF THE INVENTION

The present invention lies in a biochip comprising a large number of spots based on capture solutions arranged on a base plate, obtained by supplying, onto the base plate, a plurality of types of the capture solutions each of which specifically reacts with a specimen and each of which is used to obtain information on a structure of the specimen; wherein a plurality of the spots, which have different spot sizes, are formed on the base plate.

Accordingly, it is possible for the respective spots to suppress the dispersion of the ability to capture the specimen among the spots, which would be otherwise caused by the difference in amount of the capture immobilized on the spot or by the different abilities of the captures to capture the specimen. Thus, it is possible to suppress the dispersion of inspection results and the deterioration of quantitative performance, which would be otherwise caused by the difference in detection sensitivity among the spots.

That is, the spot, which corresponds to the capture with a small amount to be immobilized on the base plate or which corresponds to the capture with a low ability to capture the specimen, is increased in size, generally in diameter of a circular configuration. Accordingly, the detection sensitivity per one spot can be increased. As a result, it is possible to uniformize the detection sensitivities of all of the spots.

In another aspect, the present invention has the following feature. That is, when a plurality of the spots are formed for captures of an identical type on a single sheet of the base plate, then the plurality of the spots, which have different spot sizes on the base plate respectively, are formed for the captures of the identical type.

When the construction as described above is adopted, it is possible to recognize the degree of the reaction corresponding to the size of the spot, in addition to a digital inspection result to indicate whether or not the reaction occurs with respect to the captures of the identical type. Thus, it is possible to obtain an analog inspection result for the specimen. Of course, the analog inspection result can be theoretically obtained by detecting, in an analog manner, the amount of a probe which reacts with the capture immobilized in one spot. However, actually, such a procedure cannot be executed due to the restriction including, for example, the detection sensitivity of the detection equipment, the resolution, and the reaction efficiency.

Therefore, the analog analysis can be performed by combining the plurality of spots using the plurality of spots having the different sizes of the spots on the base plate respectively for the captures of the identical type as performed in the present invention, although the detection of a each spot is performed in a digital manner.

In still another aspect, the present invention lies in a biochip comprising a large number of spots based on capture solutions arranged on a base plate, obtained by supplying, onto the base plate, a plurality of types of the capture solutions each of which specifically reacts with a specimen and each of which is used to obtain information on a structure of the specimen; wherein a plurality of the spots are formed, in which an amount of a capture per unit area immobilized in each of the spots differs.

Accordingly, it is possible for the respective spots to suppress the dispersion of the ability to capture the specimen among the spots, which would be otherwise caused by the different abilities of the captures to capture the specimen, in the same manner as in the case in which the sizes of the spots differ as described above. Thus, it is possible to suppress the dispersion of inspection results and the deterioration of quantitative performance, which would be otherwise caused by the difference in detection sensitivity among the spots. That is, the concentration of the capture solution to be supplied is increased for the spot which corresponds to the capture with a low ability to capture the specimen. Accordingly, the amount of the capture immobilized on the spot is increased per unit area, and the detection sensitivity per one spot is increased. As a result, it is possible to uniformize the detection sensitivities of all of the spots.

The method of changing the amount per unit area of the capture amount immobilized on one spot may be also carried out by changing the concentration of the capture solution to be supplied as described above. Alternatively, the method may be also carried out by changing the capture amount to be supplied to one spot.

There is a certain upper limit for the capture amount immobilized per one spot. Therefore, the capture solution having a concentration lower than an average of all spots, or the capture solution in an amount smaller than an average of all spots is supplied for the spot corresponding to the capture having the high ability to capture the specimen. On the other hand, the capture solution at a concentration and/or in an amount corresponding to the upper limit of the capture amount to be immobilized or corresponding to an amount exceeding the upper limit is supplied to the spot corresponding to the capture having the low ability to capture the specimen.

Mistakes tend to be caused when the concentration and the amount of the capture solution to be supplied are individually managed for the respective spots as described above. It is advantageous to simplify the step to be as simple as possible. In such a case, when the capture solution is supplied onto the base plate by using an ink-jet method as described later on, it is preferable that the amount of solution to be supplied is changed by changing the number of discharge times for one spot.

The method of suppressing the dispersion of the ability to capture the specimen among the spots caused by the captures having the different abilities to capture the specimen by changing the concentration of the capture solution to be supplied or by changing the amount of the capture to be supplied for one spot is also used to reduce the dispersion when the immobilization ratio of the capture to be immobilized per one spot differs.

That is, as for the formation of the spot corresponding to the capture having the low immobilization ratio, it is possible to suppress the dispersion of the immobilization efficiency among the respective spots by increasing the concentration of the capture solution to be supplied, or by increasing the amount of the capture solution to be supplied per one spot.

In still another aspect of the present invention, when a plurality of spots of the captures of an identical type are formed on one sheet of the base plate, the plurality of the spots, which have different amounts of the capture per unit area immobilized on the base plate respectively, are formed for the captures of the identical type.

When the construction as described above is adopted, it is possible to recognize the degree of the reaction corresponding to the amount of the capture immobilized per unit area of the spot, in addition to a digital inspection result to indicate whether or not the reaction occurs with respect to the capture, concerning the captures of the identical type in the same manner as in the case in which the sizes of the spots differ as described above. Thus, it is possible to obtain an analog inspection result for the specimen. Of course, the analog inspection result can be theoretically obtained by detecting, in an analog manner, the amount of a probe which reacts with the capture immobilized in one spot. However, actually, such a procedure cannot be executed due to the restriction including, for example, the detection sensitivity of the detection equipment, the resolution, and the reaction efficiency. Therefore, the analog analysis can be performed by combining the plurality of spots, although the detection itself is performed in a digital manner with the plurality of spots having the different amounts of the capture immobilized per unit area of each of the spots on the base plate respectively for the captures of the identical type as performed in the present invention.

In still another aspect, the present invention lies in a biochip comprising a large number of spots based on capture solutions arranged on a base plate, obtained by supplying, onto the base plate, a plurality of types of the capture solutions each of which specifically reacts with a specimen and each of which is used to obtain information on a structure of the specimen; wherein the spots, which are composed of different types of the captures, are formed at an identical spot formation position. In this case, it is possible to greatly reduce the arrangement area for the spots, and it is possible to miniaturize the biochip itself.

In still another aspect, the present invention lies in a biochip comprising a large number of spots based on capture solutions arranged on a base plate, obtained by supplying, onto the base plate, a plurality of types of the capture solutions each of which specifically reacts with a specimen and each of which is used to obtain information on a structure of the specimen; wherein each of the spots has a shape of a substantially circular configuration, and a ratio between a major axis and a minor axis of the substantially circular configuration is not less than 0.9 and not more than 1.1.

Accordingly, the dispersion of the shape of each of the spots is reduced. It is easy to recognize the fluorescence light emission from the spot with a CCD camera or the like, and the inspection accuracy is improved. Especially, owing to the fact that the planar configuration of the spot is substantially circular, it is possible to avoid flowing the sample solution from the spot during the formation of the spot, and it is possible to prevent the sample solutions in the plurality of spots from being mixed with each other. In this case, it is also preferable that the spots are arranged at least in a zigzag configuration, and a ratio of an area in which the spot is not deposited with respect to an inspection effective area on the base plate is not more than 22%. In this case, it is possible to achieve a high degree of concentration of spots. Accordingly, it is possible to perform detailed genetic analysis for a large amount of a biochemical sample at once.

It is preferable for the biochip described above that the spots based on the sample solution are formed by means of an ink-jet system.

In the ink-jet system, the spot is formed by discharging the capture solution into the atmospheric air and allowing the capture solution to arrive at the base plate as a target. Therefore, the shape of the spot is a circular configuration which is approximate to a perfect circle owing to the surface tension of the sample. Therefore, the dispersion of the shape is reduced for the respective spots. Owing to the fact that the force of discharge and the number of times of discharge per unit time (discharge frequency) can be electrically controlled, the amount of the capture supplied to one spot on the base plate can be freely changed. Thus, the size of the spot and the amount of the capture per unit volume immobilized in the spot on the base plate can be varied.

Especially, the amount of the capture per unit volume is preferably varied by discharging and supplying the capture solution a plurality of times to one spot on the base plate in accordance with the ink-jet system. That is, the capture solution is discharged and supplied a plurality of times in a divided manner without discharging and supplying a large amount of the capture solution at once. Further, the discharge interval is adjusted so that a previously formed spot is not widened in spot diameter due to superimposition of the capture solution subsequently discharged. Accordingly, the amount of the capture supplied to the spot can be increased or decreased without changing the size of the spot. Thus, it is possible to vary the capture density per unit area.

BRIEF DESCRIPTION OF THE DRAWINGS

FIG. 4 shows a block diagram illustrating steps as contents of a sample preparation step;

FIG. 6 shows a longitudinal sectional view illustrating an arrangement of the micropipette;

FIG. 16 illustrates a state in which different types of spots are formed at an identical spot formation position;

DETAILED DESCRIPTION OF THE DRAWINGS

Embodiments of the DNA microarray according to the present invention will be explained below with reference to FIGS. 1 to 18.

Figure 1:
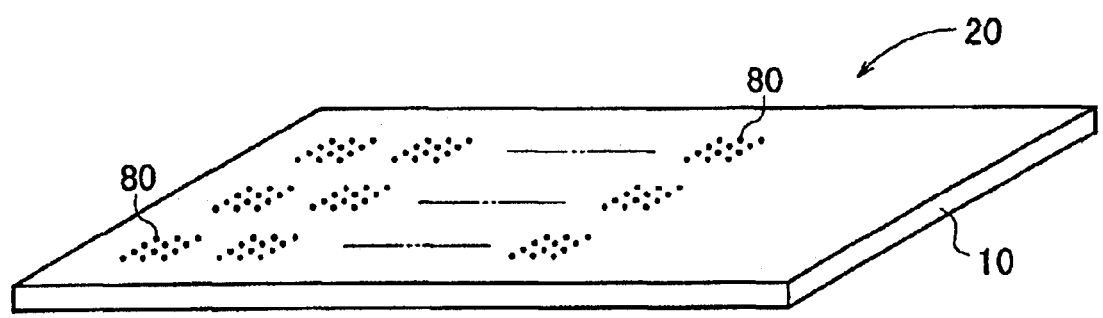
FIG. 1 shows a perspective view illustrating a DNA microarray according to an embodiment of the present invention.
Figure 2:
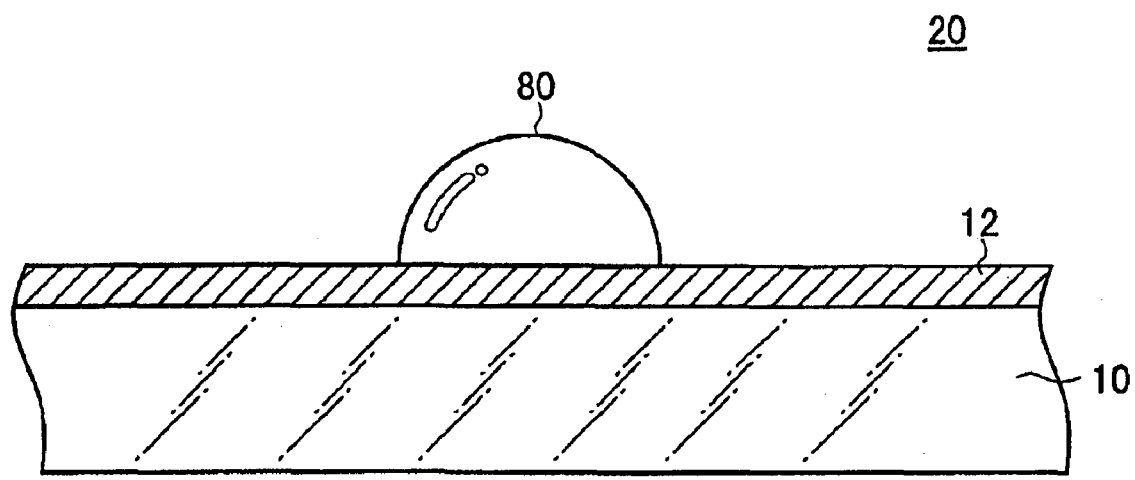
FIG. 2 shows a magnified sectional view illustrating an arrangement of the DNA microarray according to the embodiment of the present invention.

As shown in FIGS. 1 and 2, a DNA microarray 20 according to an embodiment of the present invention comprises a large number of minute spots 80 arranged on a base plate 10 by supplying (including dropwise addition) a sample solution. A poly-L-lysine layer 12 is formed on the surface of the base plate 10.

Figure 3:
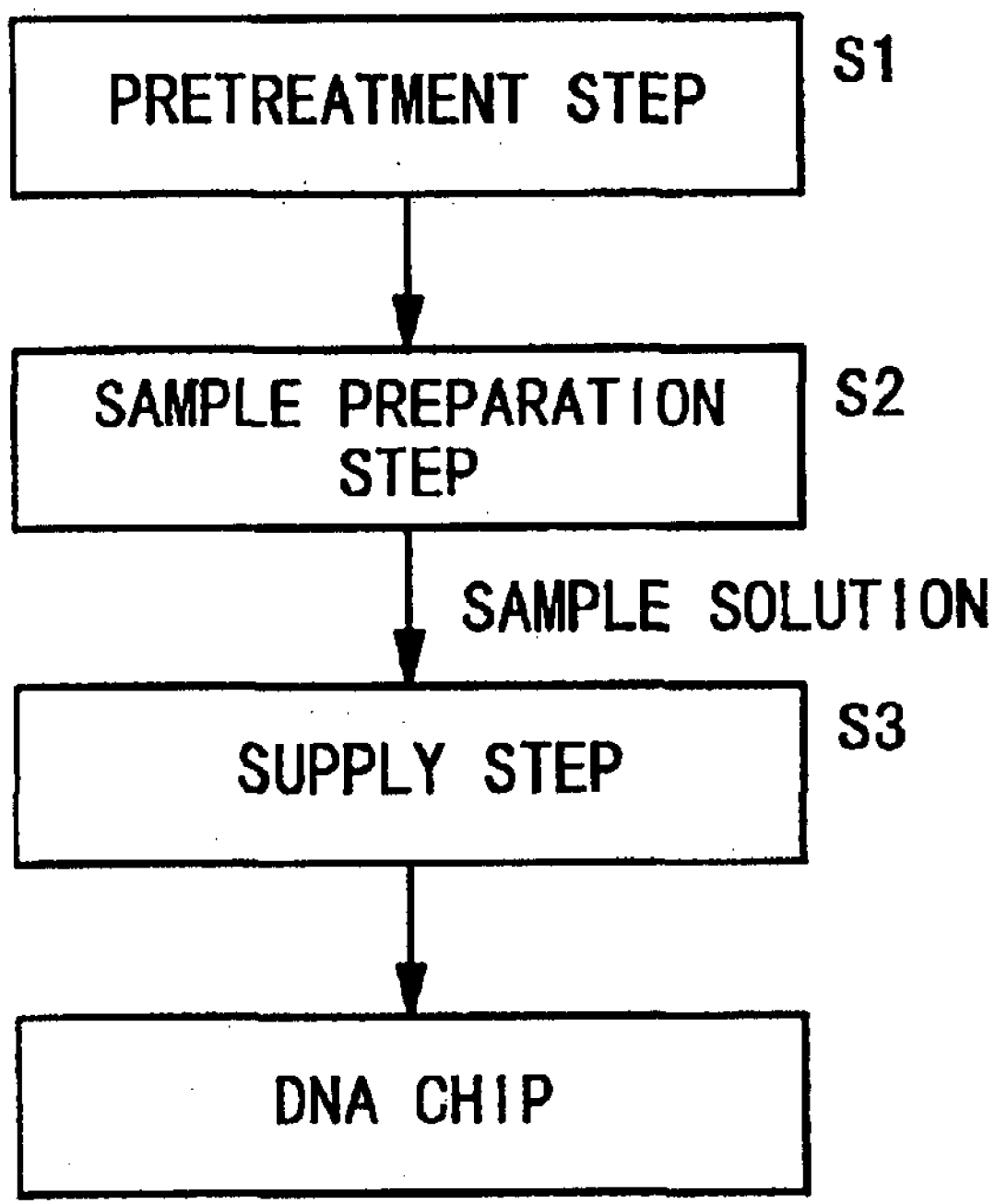
FIG. 3 shows a block diagram illustrating steps of a method of producing the DNA microarray according to the embodiment of the present invention.

The DNA microarray 20 is produced by forming the minute spots 80 by supplying the sample solution onto the base plate 10, for example, by performing production steps as shown in FIG. 3.

That is, the DNA microarray 20 is produced by performing a pretreatment step S1 of forming the poly-L-lysine layer 12 (see FIG. 2) on the surface of the base plate 10, a sample preparation step S2 of preparing the sample solution containing DNA fragment, and a supply step S3 of supplying the obtained sample solution onto the base plate 10.

As shown in FIG. 4, the sample preparation step S2 includes an amplification step S11 of performing PCR amplification for the DNA fragment to prepare a PCR product, a purification step S12 of purifying and drying the obtained PCR product to prepare DNA powder, and a mixing step S13 of dissolving the obtained DNA powder in a buffer solution.

The process will be specifically explained below. That is, in the pretreatment step S1, the base plate 10 is firstly immersed in an alkaline solution to perform slow shaking at room temperature for at least 2 hours. The alkaline solution is a solution which is obtained, for example, by dissolving NaOH in distilled water, and adding ethanol thereto, followed by being agitated until the solution is completely transparent.

After that, the base plate 10 is taken out, and it is transferred into distilled water, followed by being rinsed to remove the alkaline solution. Subsequently, the base plate 10 is immersed in a poly-L-lysine solution prepared by adding poly-L-lysine to distilled water, followed by being left to stand for 1 hour.

After that, the base plate 10 is taken out, and it is applied to a centrifugal machine to perform centrifugation so that any excessive poly-L-lysine solution is removed. Subsequently, the base plate 10 is dried at 40° C. for about minutes to obtain the base plate 10 with the poly-L-lysine layer 12 formed on the surface.

Subsequently, the sample preparation step S2 is performed. At first, 3M sodium acetate and isopropanol are added to the PCR product amplified by using a known PCR machine (amplification step S11), followed by being left to stand for several hours. After that, the PCR product solution is centrifuged with a centrifugal machine to precipitate the DNA fragments.

The precipitated DNA fragments are rinsed with ethanol, followed by centrifugation. After that, the DNA fragments are dried to produce the DNA powder (purification step S12). A certain amount of ×1 TE buffer is added to the obtained DNA powder, followed by being left to stand for several hours to completely dissolve the DNA powder (mixing step S13). Thus, the sample solution is prepared. The concentration of the sample solution at this stage is 0.1 to 10 μg/ml.

In the embodiment of the present invention, the obtained sample solution is supplied onto the base plate 10 to produce the DNA microarray 20 (supply step S3). An immobilizing solution may be mixed with the sample solution obtained by performing the sample preparation step S2. The sample solution may be diluted as well. In this case, the buffer solution described above, an aqueous solution containing water and NaCl, or an aqueous solution containing polymer may be used as a diluting solution.

When the DNA microarray 20 is produced in this embodiment, for example, a disperser 30 shown in FIGS. 5A to 7 is effectively used.

Figure 5A:
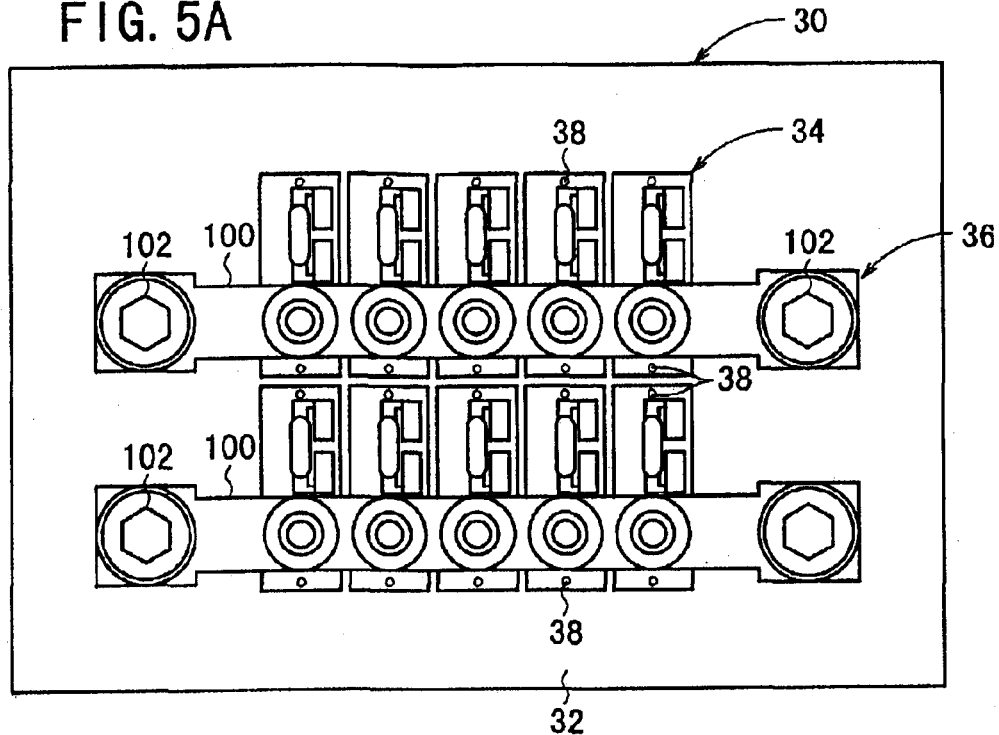
FIG. 5A shows a plan view illustrating an arrangement of a dispenser to be used for the method of producing the DNA microarray according to a first embodiment.
Figure 5B:
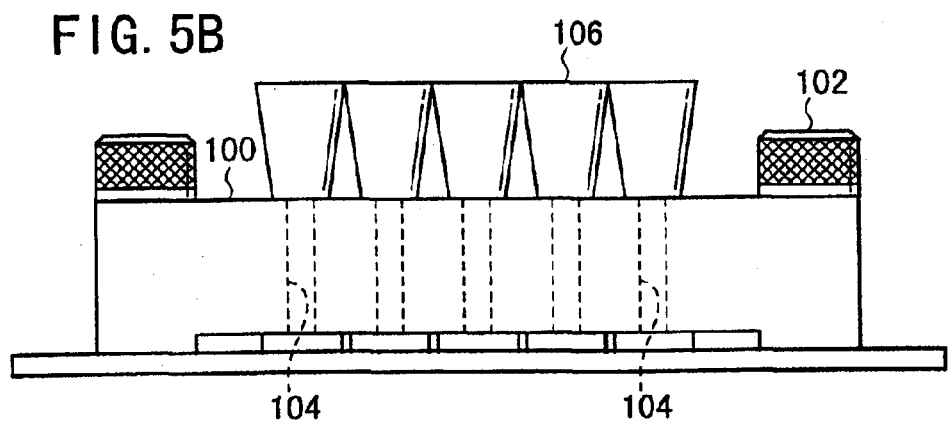
FIG. 5B shows a front view thereof.

As shown in FIGS. 5A and 5B, the dispenser 30 has the following arrangement. That is, for example, ten micropipettes 34 are arranged in five rows and two columns on an upper surface of a fixation plate 32 having a rectangular configuration. A group of the micropipettes 34 arranged in the direction of each column are fixed on the fixation plate 32 by the aid of a fixing jig 36 respectively.

Figure 5C:
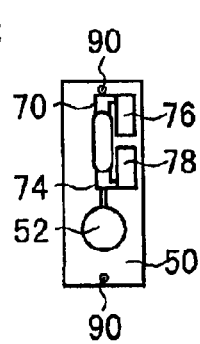
FIG. 5C shows a magnified plan view illustrating one micropipette for constructing the dispenser.

As shown in FIGS. 5C and 6, the micropipette 34 comprises a sample-pouring port 52 which is formed at the upper surface of a substrate 50 having a substantially rectangular parallelepiped-shaped configuration, a sample discharge port 54 which is formed at the lower surface of the substrate 50, a cavity 56 which is formed between the sample-pouring port 52 and the sample discharge port 54, and an actuator section 58 which is used to vibrate the substrate 50 or change the volume of the cavity 56.

Therefore, as shown in FIG. 6, through-holes 40 are provided through the fixation plate 32 at portions corresponding to the sample discharge ports 54 of the micropipettes 34 respectively. Accordingly, the sample solution, which is discharged from the sample discharge port 54 of the micropipette 34, is supplied through the through-hole 40, for example, to the base plate 20 which is fixed under the fixation plate 32.

An introducing bore 60 having a substantially L-shaped configuration with a wide opening is formed over a region ranging from the sample-pouring port 52 to the inside of the substrate 50 in the micropipette 34. A first communication hole 62 having a small diameter is formed between the introducing bore 60 and the cavity 56. The sample solution, which is poured from the sample-pouring port 52, is introduced into the cavity 56 through the introducing bore 60 and the first communication hole 62.

A second communication hole 64, which communicates with the sample discharge port 54 and which has a diameter larger than that of the first communication hole 62, is formed at a position different from that of the first communication hole 62, of the cavity 56. In the embodiment of the present invention, the first communication hole 62 is formed at the portion of the lower surface of the cavity 56 deviated toward the sample-pouring port 52. The second communication hole 64 is formed at the position of the lower surface of the cavity 56 as well corresponding to the sample discharge port 54.

Further, in the this embodiment, the portion of the substrate 50, with which the upper surface of the cavity 56 makes contact, is thin-walled to give a structure which tends to undergo the vibration with respect to the external stress so that the portion functions as a vibrating section 66. The actuator section 58 is formed on the upper surface of the vibrating section 66.

The substrate 50 is constructed by laminating a 5 plurality of green sheets made of zirconia ceramics (first thin plate layer 50A, first spacer layer 50B, second thin plate layer 50C, second spacer layer 50D, and third thin plate layer 50E) followed by being sintered into one unit.

That is, the substrate 50 is constructed by laminating the thin-walled first thin plate layer 50A which is formed with a window for constructing the sample-pouring port 52 and which constitutes a part of the vibrating section 66, the thick-walled first spacer layer 50B which is formed with a part of the introducing bore 60 and a plurality of windows for constructing the cavity 56 respectively, the thin-walled second thin plate layer 50C which is formed with a part of the introducing bore 60 and a plurality of windows for constructing parts of the second communication hole 64 and the first communication hole 62 respectively, the thick-walled second spacer layer 50D which is formed with a plurality of windows for constructing a part of the introducing bore 60 and a part of the second communication hole 64 respectively, and the thin-walled third thin plate layer 50E which is formed with a window for constructing the sample discharge port 54, followed by being sintered into one unit.

The actuator section 58 is constructed to have the vibrating section 66 described above as well as a lower electrode 70 which is directly formed on the vibrating section 66, a piezoelectric layer 72 which is composed of, for example, a piezoelectric/electrostrictive layer or an anti-ferroelectric layer formed on the lower electrode 70, and an upper electrode 74 which is formed on the upper surface of the piezoelectric layer 72.

As shown in FIG. 5C, the lower electrode 70 and the upper electrode 74 are electrically connected to an unillustrated driving circuit via a plurality of pads 76, 78 which are formed on the upper surface of the substrate 50 respectively.

The micropipette 34 constructed as described above is operated as follows. That is, when an electric field is generated between the upper electrode 74 and the lower electrode 70, then the piezoelectric layer 72 is deformed, and the vibrating section 66 is deformed in accordance therewith. Accordingly, the volume of the cavity (pressurizing chamber) 56 contacting with the vibrating section 66 is decreased.

When the volume of the cavity 56 is decreased, the sample solution charged in the cavity 56 is discharged at a predetermined speed from the sample discharge port 54 which communicates with the cavity 56. As shown in FIG. 1, it is possible to prepare the DNA microarray 20 in which the sample solutions discharged from the micropipettes 34 are aligned and fixed as minute spots 80 on the base plate 50 such as a microscopic slide glass.

In this arrangement, when the arrangement pitch of the sample discharge ports 54 in the dispenser 30 is larger than the arrangement pitch of the minute spots 80 formed on the base plate 10, the sample solution is supplied while shifting the supply position for the dispenser 30.

An apparatus structure based on the so-called ink-jet system may be adopted as the structure in which the volume of the cavity 56 is decreased in accordance with the driving of the actuator section 58 (see Japanese Laid-Open Patent Publication No. 6-40030).

The cavity (pressurizing chamber) 56 is preferably formed to have such a flow passage dimension that the sample solution containing DNA fragments or the like is moved in laminar flow.

Figure 7:
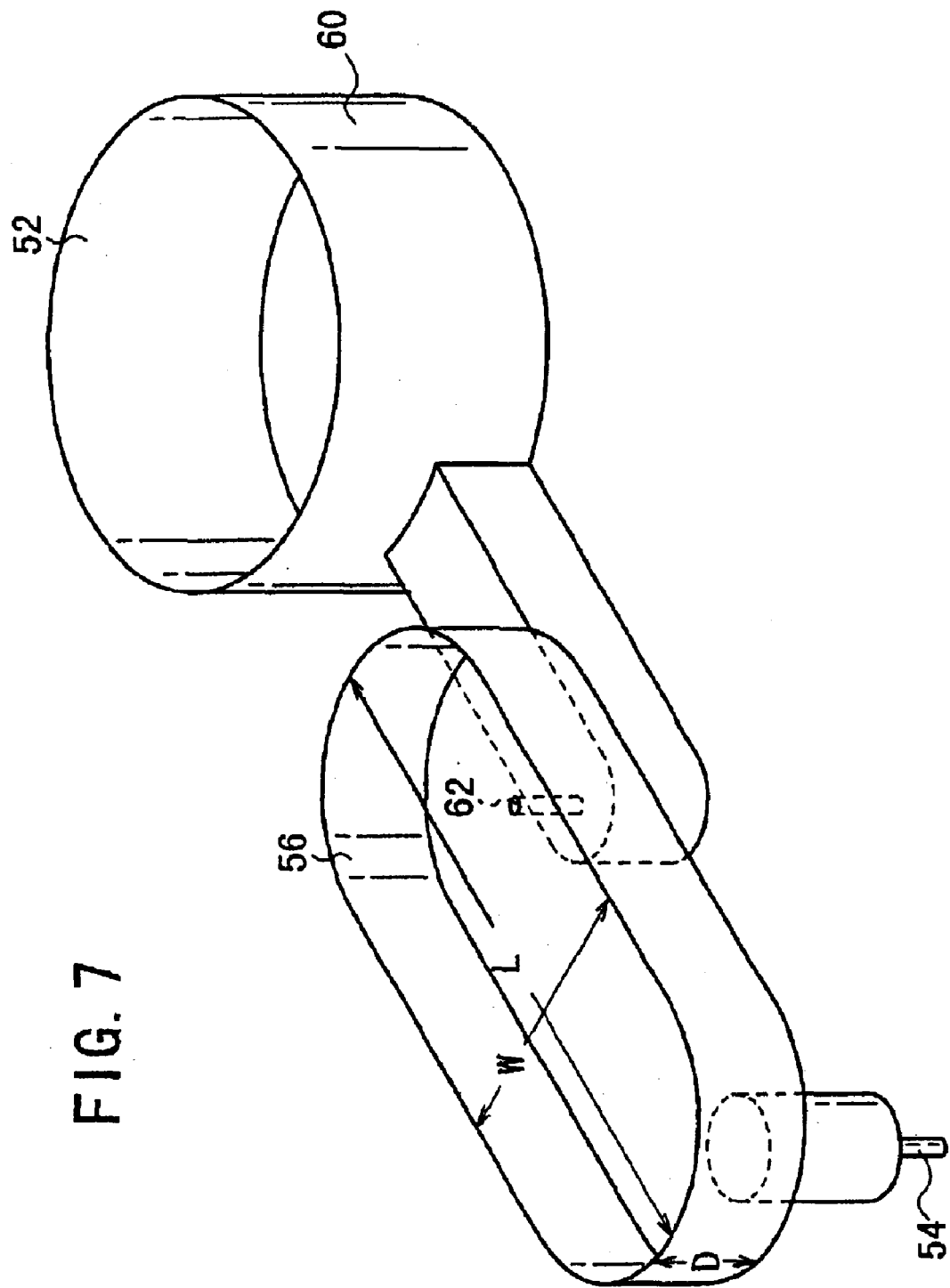
FIG. 7 shows the shape of a flow passage including a cavity formed in a substrate of the micropipette.

That is, the dimension of the cavity 56 differs depending on the type of the sample, the size of liquid droplets to be prepared, and the density of formation. However, for example, when DNA fragments of base pairs having a length of about 1 to 10,000 bp are dissolved in a buffer solution (TE buffer) at a concentration of 0.5 $\mu g/\mu$liter to obtain a sample which is dripped at a pitch of several hundreds $\mu$m to give a liquid droplet diameter of several hundreds $\mu$m$\phi$, then it is preferable that the cavity length (L) is 1 to 5 mm, the cavity width (W) is 0.1 to 1 mm, and the cavity depth (D) is 0.1 to 0.5 mm as shown in FIG. 7. It is preferable that the inner wall of the cavity 56 is smooth without involving any projection to disturb the flow. It is preferable that the material of the cavity 56 is made of ceramics which has good affinity with respect to the sample solution.

When the shape as described above is adopted, the cavity 56 can be used as a part of the flow passage ranging from the sample-pouring port 52 to the sample discharge port 54. The sample can be introduced to the sample discharge port 54 without disturbing the flow of the sample solution which is moved from the sample-pouring port 52 via the introducing bore 60 and the first communication hole 62 to the inside of the cavity 56.

As shown in FIG. 5A, a plurality of pins 38 for positioning and fixing the micropipettes 34 are provided on the upper surface of the fixation plate 32. When the micropipette 34 is fixed on the fixation plate 32, the micropipette 34 is placed on the fixation plate 32 while inserting the pins 38 of the fixation plate 32 into positioning holes 90 (see FIG. 5C) provided at the both sides of the substrate 50 of the micropipette 34. Thus, a plurality of micropipettes 34 are automatically positioned with a predetermined array arrangement.

Each of the fixing jigs 36 has a holder plate 100 for pressing the plurality of micropipettes 34 against the fixation plate 32. Insertion holes for inserting screws 102 thereinto are formed through both end portions of the holder plate 100. When the screws 102 are inserted into the insertion holes, and they are screwed into the fixation plate 32, then the plurality of micropipettes 34 can be pressed against the fixation plate 32 by the aid of the holder plate 100 at once. One unit is constructed by the plurality of micropipettes 34 which are pressed by one holder plate 100. The example shown in FIG. 5A is illustrative of the case in which one unit is constructed by the five micropipettes 34 which are arranged in the direction of the column.

The holder plate 100 is formed with introducing holes 104 (see FIG. 5B) which are used to supply the sample solutions to the portions corresponding to the sample-pouring ports 52 of the respective micropipettes 34 respectively when the plurality of micropipettes 34 are pressed. Tubes 106 for introducing the sample solution to the introducing holes 104 respectively are held at upper end portions of the respective introducing holes 104.

Considering the realization of the efficient wiring operation, it is preferable that the width of the holder plate 100 resides in such a dimension that the pads 76, 78 connected to the respective electrodes 70, 74 of the actuator section 58 are faced upwardly when the plurality of micropipettes 34 are pressed against the fixation plate 32.

As described above, the dispenser 30 described above is constructed such that the plurality of micropipettes 34 each having the sample-pouring port 52 and the sample discharge port 54 are provided in an upstanding manner with the respective sample discharge ports 54 directed downwardly.

That is, the respective micropipettes 34 are aligned and arranged such that the respective sample-pouring ports 52 are disposed on the upper side, the sample discharge ports 54 are disposed on the lower side, and the respective sample discharge ports 54 are aligned two-dimensionally. Sample solutions of mutually different types are discharged from the sample discharge ports 54 respectively.

Figure 8:
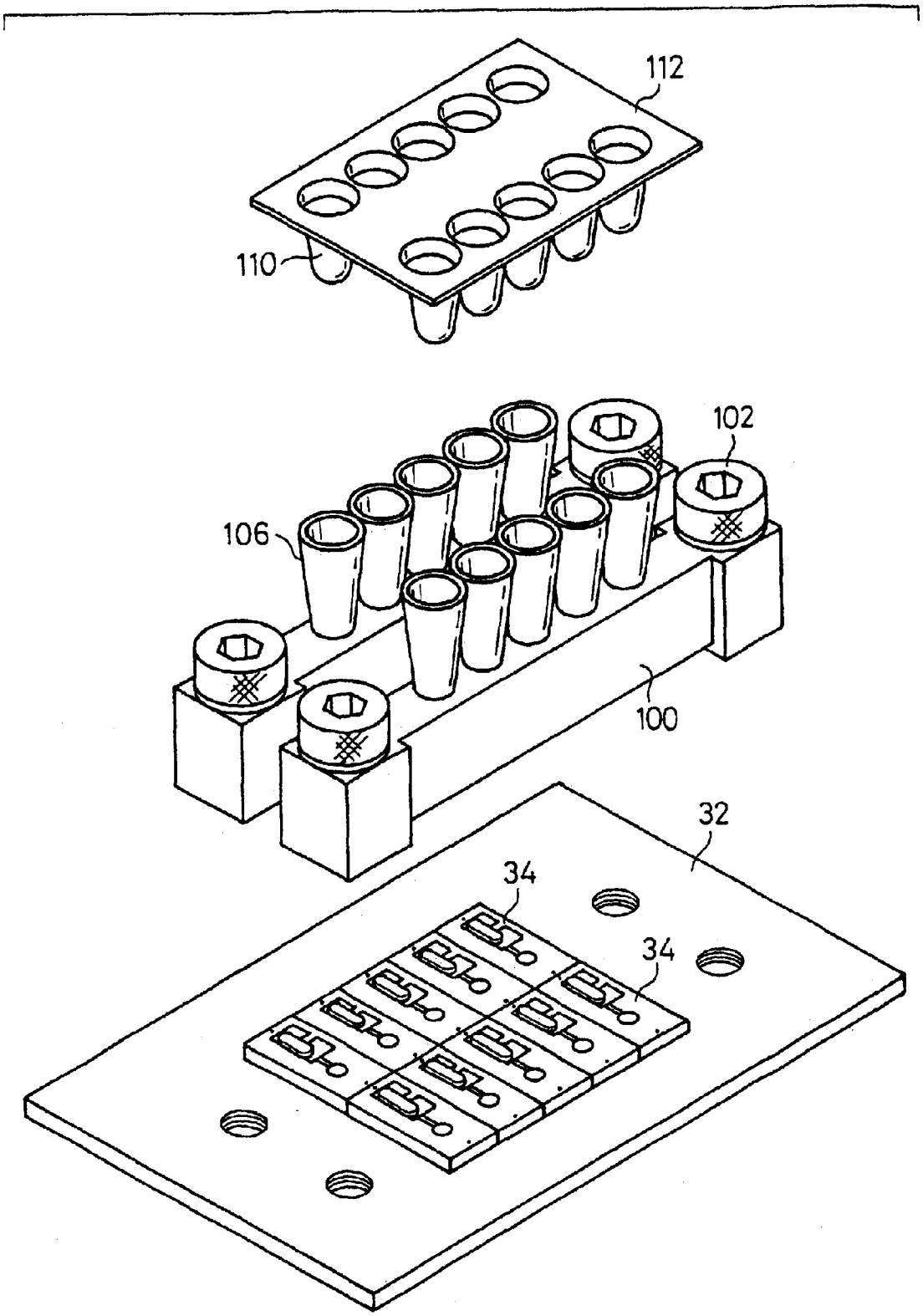
FIG. 8 shows an exploded perspective view illustrating the dispenser together with a cartridge.

When the dispenser 30 constructed as described above is used, an automatic dispenser or the like, which is constructed by combining an XY robot and the dispenser, is generally used for a method of supplying the sample solutions of mutually different types corresponding to the respective sample-pouring ports 52. However, as shown in FIG. 8, for example, a method is available, which is based on the use of a cartridge 112 arranged with a large number of recesses (storage sections) 110 each having a substantially V-shaped cross section. For this method, for example, the following procedure is available. That is, the sample solutions of the different types are poured into the respective recesses 110 of the cartridge 112 respectively. The cartridge 112 is attached so that the respective recesses 110 correspond to the tubes 106 respectively. The bottoms of the respective recesses 110 are opened with needles or the like. Accordingly, the sample solutions in the respective recesses 110 are supplied via the tubes 106 to the respective micropipettes 34.

When the tubes 106 are not used, for example, the following method is available. That is, the cartridge 112 is attached so that the respective recesses 110 correspond to the respective introducing holes 104 of the fixing jig 36 respectively. The bottoms of the respective recesses 110 are opened with needles or the like. Accordingly, the sample solutions in the respective recesses 110 are supplied via the introducing holes 104 to the respective micropipettes 34. Alternatively, needles or the like may be formed in the vicinity of the respective introducing holes 104 of the fixing jig 36 beforehand so that the respective recesses 110 may be opened simultaneously with the attachment of the cartridge 112 to the fixing jig 36.

Alternatively, it is also preferable to add a mechanism for feeding the gas or the like under the pressure after the opening to forcibly extrude the sample solutions. Further alternatively, it is also preferable to add a mechanism for making aspiration from the discharge ports of the respective micropipettes. It is desirable to provide a mechanism for washing the space ranging from the sample-pouring port 52 to the sample discharge port 54 formed in the substrate 50 of each of the micropipettes 34, for example, in order that several thousands to several tens thousands types or many kinds of DNA fragments are discharged as the minute spots 80 with good purity without involving any contamination.

In the example shown in FIG. 5A, the both ends of the holder plate 100 are tightened to the fixation plate 20 by the aid of the screws 102. However, the holder plate 100 may be fixed in accordance with other methods based on the mechanical procedure by using, for example, an adhesive or the like, as well as screws and springs.

As described above, the substrate 50 for constructing the micropipette 34 is formed of ceramics, for which it is possible to use, for example, fully stabilized zirconia, partially stabilized zirconia, alumina, magnesia, and silicon nitride.

Among them, the fully stabilized/partially stabilized zirconia is used most preferably, because the mechanical strength is large even in the case of the thin plate, the toughness is high, and the reactivity with the piezoelectric layer 72 and the electrode material is low.

When the fully stabilized/partially stabilized zirconia is used as the material, for example, for the substrate 50, it is preferable that at least the portion (vibrating section 66), on which the actuator section 58 is formed, contains an additive such as alumina and titania.

Those usable as the piezoelectric ceramic for the piezoelectric layer 72 for constructing the actuator section 58 include, for example, lead zirconate, lead titanate, lead magnesium niobate. lead magnesium tantalate, lead nickel niobate, lead zinc niobate, lead manganese niobate, lead antimony stannate, lead manganese tungstate, lead cobalt niobate, and barium titanate, as well as composite ceramics containing components obtained by combining any of them. However, in the embodiment of the present invention, a material containing a major component composed of lead zirconate, lead titanate, and lead magnesium niobate is preferably used, for following reason.

That is, such a material has a high electromechanical coupling factor and a high piezoelectric constant. Additionally, such a material has low reactivity with the substrate material during the sintering of the piezoelectric layer 72, making it possible to stably form the product having a predetermined composition.

Further, in the embodiment of the present invention, it is also preferable to use ceramics obtained by appropriately adding, to the piezoelectric ceramics described above, for example, oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and stannum, or a combination of any of them, or other compounds.

For example, it is also preferable to use ceramics containing a major component composed of lead zirconate, lead titanate, and lead magnesium niobate, and further containing lanthanum and/or strontium.

On the other hand, it is preferable that the upper electrode 74 and the lower electrode 70 of the actuator section 58 are made of metal which is solid at room temperature and which is conductive. For example, it is possible to use metal simple substance of, for example, aluminum, titanium, chromium, iron, cobalt, nickel, copper, zinc, niobium, molybdenum, ruthenium, palladium, rhodium, silver, stannum, tantalum, tungsten, iridium, platinum, gold, and lead, or alloy obtained by combining any of them. It is also preferable to use a cermet material obtained by dispersing, in the metal described above, the same material as that of the piezoelectric layer 72 or the substrate 50.

Next, explanation will be made with reference to FIGS. 9 to 12 for several methods for producing the DNA microarray 20 by using the dispenser 30.

Figure 9:
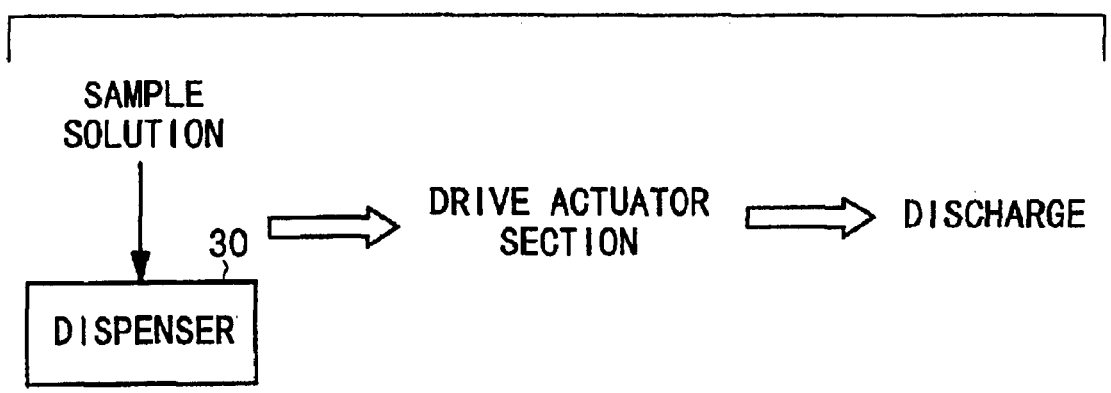
FIG. 9 illustrates a first method adopted when the DNA microarray is produced by using the dispenser.

At first, a first method is shown in FIG. 9. That is, mutually different types of sample solutions are charged from the respective tubes 106 via the introducing holes 104 of the fixing jig 36 into the cavities 56 of the respective micropipettes 34 respectively. Subsequently, the respective actuator sections 58 are driven to discharge the sample solutions from the sample discharge ports 54 of the respective micropipettes 34. As for the method of charging the solution into the cavity 56, the solution may be poured in accordance with the capillary force of the solution introduced from the sample-pouring port 52. However, it is reliable to adopt a method in which the solution is charged by means of vacuum aspiration through the sample discharge port 54.

As for the voltage waveform to be applied to the respective electrodes 70, 74 of the actuator section 58, when the actuator section 58 is subjected to the ON operation to decrease the volume of the cavity 56, a pulsed voltage is applied to the respective electrodes 70, 74. In this case, the deformation of the vibrating section 66 is increased by increasing the amplitude of the pulse, and the discharge force and the discharge amount of the sample solution are also increased corresponding thereto. When a plurality of pulses are applied for a certain period, a large number of sample solutions each having a small amount can be discharged by shortening the pulse cycle and decreasing the amplitude of each pulse.

Especially, when it is required to improve the accuracy of the control of the amount of the sample to be supplied per one spot when the DNA microarray is produced by using a plurality of micropipettes, it is preferable to adopt the method of discharging a large number of sample solutions in a small amount, for the following reason. That is, the number of times of discharge can be completely controlled electrically, and hence the minute dispersion of the discharge ability (discharge amount) for each of the micropipettes can be corrected by the number of times of discharge.

During this process, when the supply position is appropriately changed, the droplets of the supplied sample solution are combined (integrated) on the base plate 10 to form the sample solution having one spot diameter. Further, it is possible to realize a uniform spot diameter formed on the base plate 10 by controlling the number of supply operations, the supply position, and the amount of one time supply, depending on the type of the sample solution to be supplied.

Figure 10:
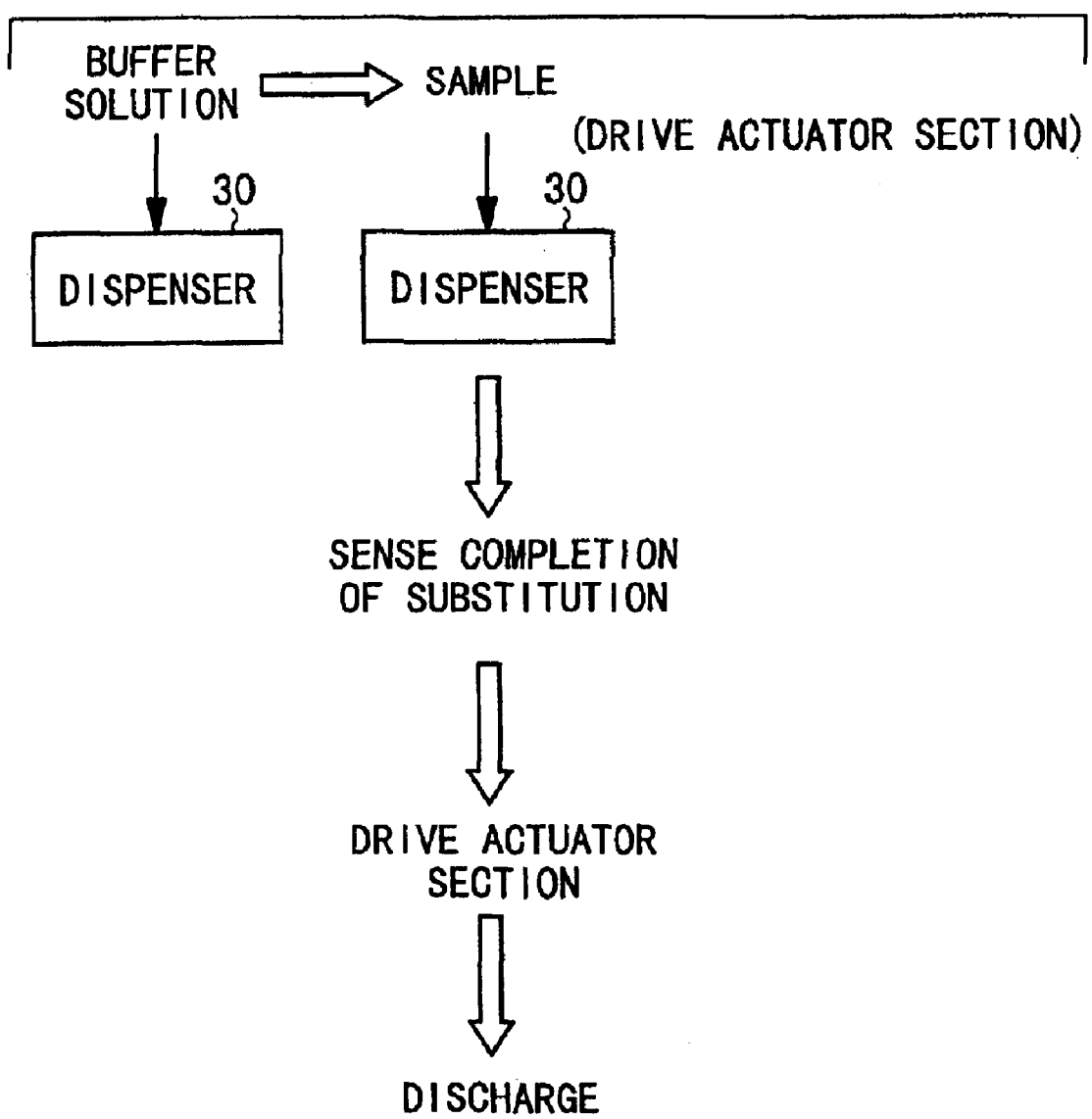
FIG. 10 illustrates a second method adopted when the DNA microarray is produced by using the dispenser.
Figure 11:
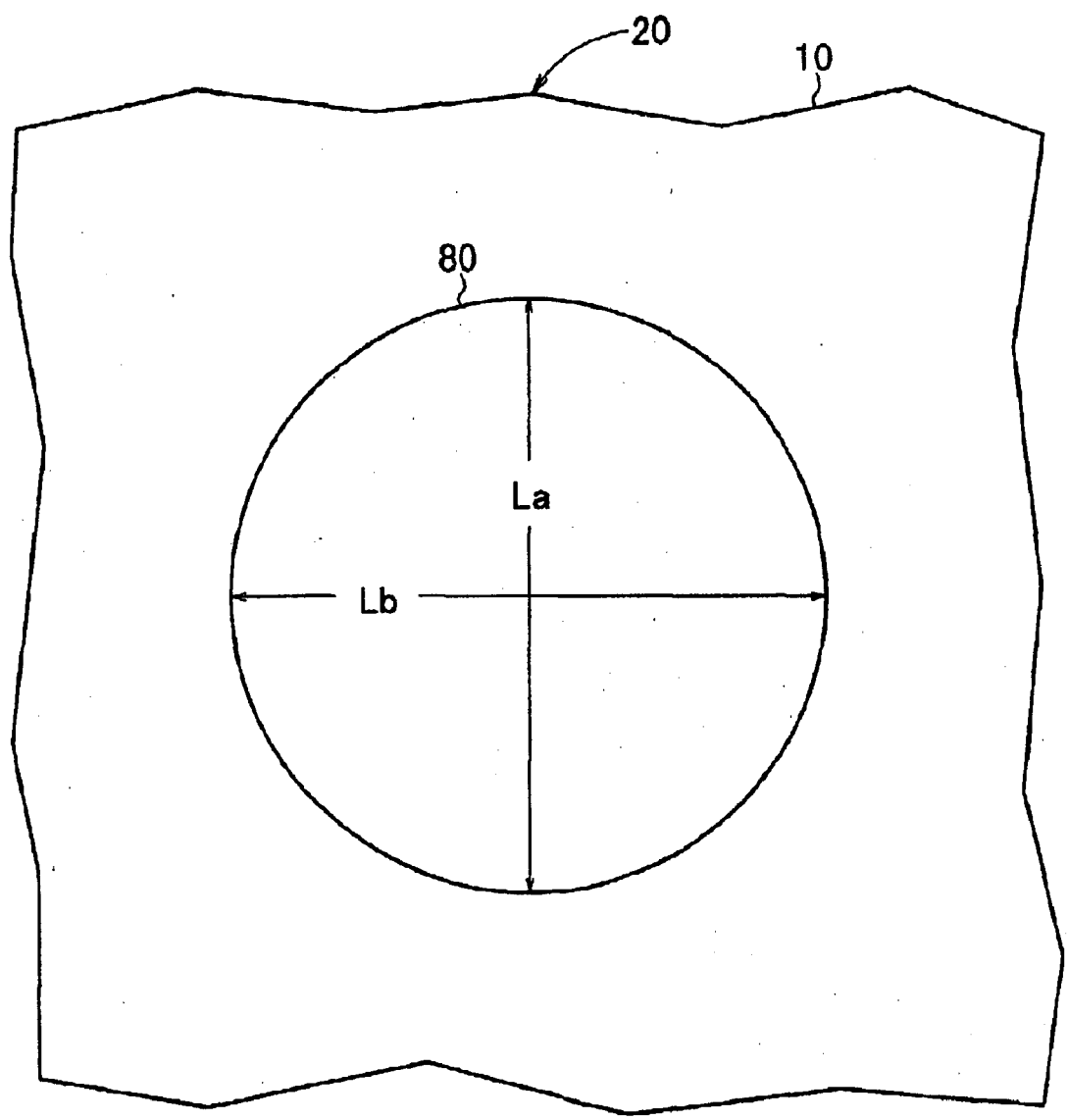
FIG. 11 illustrates a state of formation of a spot of the DNA microarray according to the embodiment of the present invention.

Next, explanation will be made for a second method based on the use of the dispenser 30. The second method is shown in FIG. 10. That is, a substitution solution such as a buffer solution, an aqueous solution containing NaCl, and an aqueous solution containing polymer is charged into the cavity 56 of each of the micropipettes 34 from each of the tubes 106 via the introducing hole 104 of the fixing jig 36 respectively. Subsequently, the sample is poured into the cavity 56 from the sample-pouring port 52 while effecting the laminar flow substitution to wait for the completion of the substitution thereafter. After that, the actuator section 58 is driven to discharge and supply the sample solution onto the base plate 10.

It is preferable that the completion of the laminar flow substitution of the sample in the cavity 56 is recognized by sensing the change of the fluid characteristic in the cavity 56.

It is preferable that the substitution between the substitution solution and the sample solution in the cavity 56 is performed in a form of the laminar flow. However, when the type of the sample is changed, or when the movement speed of the liquid is extremely fast, then it is not necessarily indispensable to use the laminar flow at portions of the cavity 56 in the vicinity of the first communication hole 62. In this case, the purge amount of the sample solution is increased due to the mixing of the sample and the substitution solution. However, it is possible to suppress the increase in the purge amount to be minimum by judging the completion of the substitution by sensing the change of the fluid characteristic in the cavity 56.

In the present invention, the change of the fluid characteristic in the cavity 56 is recognized by applying a voltage in such a degree as to excite the vibration in the actuator section 58, and detecting the change of the electric constant caused by the vibration. Such a procedure for sensing the change of the fluid characteristic is disclosed, for example, in Japanese Laid-Open Patent Publication No. 8-201265.

Specifically, the electric connection from a power source for driving the discharge is separated from the actuator section 58 at a predetermined interval by using a relay. Simultaneously, a means for measuring the resonance frequency is connected by using the relay. At this point of time, the impedance or the resonance characteristic such as the resonance frequency or the attenuation factor is electrically measured.

Accordingly, it is possible to recognize, for example, whether or not the viscosity and the specific gravity of the liquid are those of the objective sample (liquid containing the DNA fragment or the like). That is, as for each of the micropipettes 34, the micropipette 34 itself functions as a sensor. Therefore, it is also possible to simplify the structure of the micropipette 34.

The actuator section 58 is driven under a driving condition corresponding to the amount of liquid droplets suitable for the required spot diameter, and the sample solution is repeatedly supplied. Accordingly, the DNA microarray 20 is produced. Usually, when one minute spot 80 is formed, one to several hundreds of droplet or droplets are discharged from the micropipette 34.

When the amount of the sample in the sample-pouring port 52 is decreased, the discharge is continued by adding the buffer solution so that no bubble enters the inside of the flow passage. Accordingly, all of the sample solution can be used without allowing the sample solution to remain in the micropipette 34. The completion of the substitution from the sample to the substitution solution (completion of the sample discharge) is confirmed by detecting the viscosity and the specific gravity of the liquid by using the actuator section 58 in the same manner as described above.

It is preferable to use the substitution solution and the sample solution such that the dissolved gas in the solution is previously removed by performing the degassing operation. When such a solution is used, if any bubble obstructs the flow passage at an intermediate portion to cause the defective charge upon the charge of the solution into the flow passage of the micropipette 34, then the inconvenience can be avoided by dissolving the bubble in the solution. Further, no bubble is generated in the fluid during the discharge, and no defective discharge is caused as well.

In the second method described above, the substitution solution such as a buffer solution, an aqueous solution containing NaCl, and an aqueous solution containing polymer is poured from the sample-pouring port 52 into the cavity 56 while discharging the sample solution, and the sample solution remaining in the cavity 56 is completely discharged for pouring the next sample.

When it is sensed whether or not the sample solution remains in the cavity 56 (whether or not the discharge can be effected as the sample solution), the recognition can be also made by sensing the change of the fluid characteristic in the cavity 56. In this case, a mechanism for detecting the completion of the substitution can be used to extremely decrease the purge amount of the sample which is not used and improve the efficiency of the use of the sample solution.

It is also preferable that when the sample is charged from the sample-pouring port 52 to the cavity 56, the interior of the cavity 56 is substituted with the sample from the sample-pouring port 52 while driving the actuator section 58. In this procedure, the interior of the cavity 56 can be substituted in a reliable manner with the inexpensive substitution solution beforehand. As a result, it is possible to completely avoid the occurrence of any defective discharge, and it is possible to efficiently discharge the expensive sample.

Further, the following procedure may be adopted. That is, the substitution solution such as a buffer solution, an aqueous solution containing NaCl, and an aqueous solution containing polymer is charged into the cavity 56. The amount of the substitution solution existing in the cavity 56 and in the sample-pouring port 52 is adjusted to be a predetermined amount. Subsequently, a predetermined liquid amount of the sample solution is poured from the sample-pouring port 52, and then the actuator section 58 is driven in an amount corresponding to a predetermined number of pulses to discharge the amount of the substitution solution existing in the cavity 56 and in the sample-pouring port 52.

In this manner, the amount of the substitution solution existing in the cavity 56 and in the sample-pouring port 52 is correctly discharged, and it is possible to complete the charge of the sample solution without any loss.

In the first and second methods described above, for example, as shown in FIG. 11, the planar configuration of the spot 80 formed on the base plate 10 is substantially circular. In this case, the ratio between the major axis La and the minor axis Lb of each of the spots 80 is not less than 0.9 and not more than 1.1.

Accordingly, the dispersion of the shapes of the respective spots 80 is reduced. Even when unknown DNA is inspected, it is easy to recognize the fluorescence light emission from the spot 80 with a CCD camera or the like. Thus, the inspection accuracy is improved. Especially, since the planar configuration of the spot 80 is substantially circular, it is possible the avoid the flow of the sample solution during the formation of the spot 80, and it is possible to prevent the sample solutions in the plurality of spots 80 from being mixed with each other.

Figure 12:
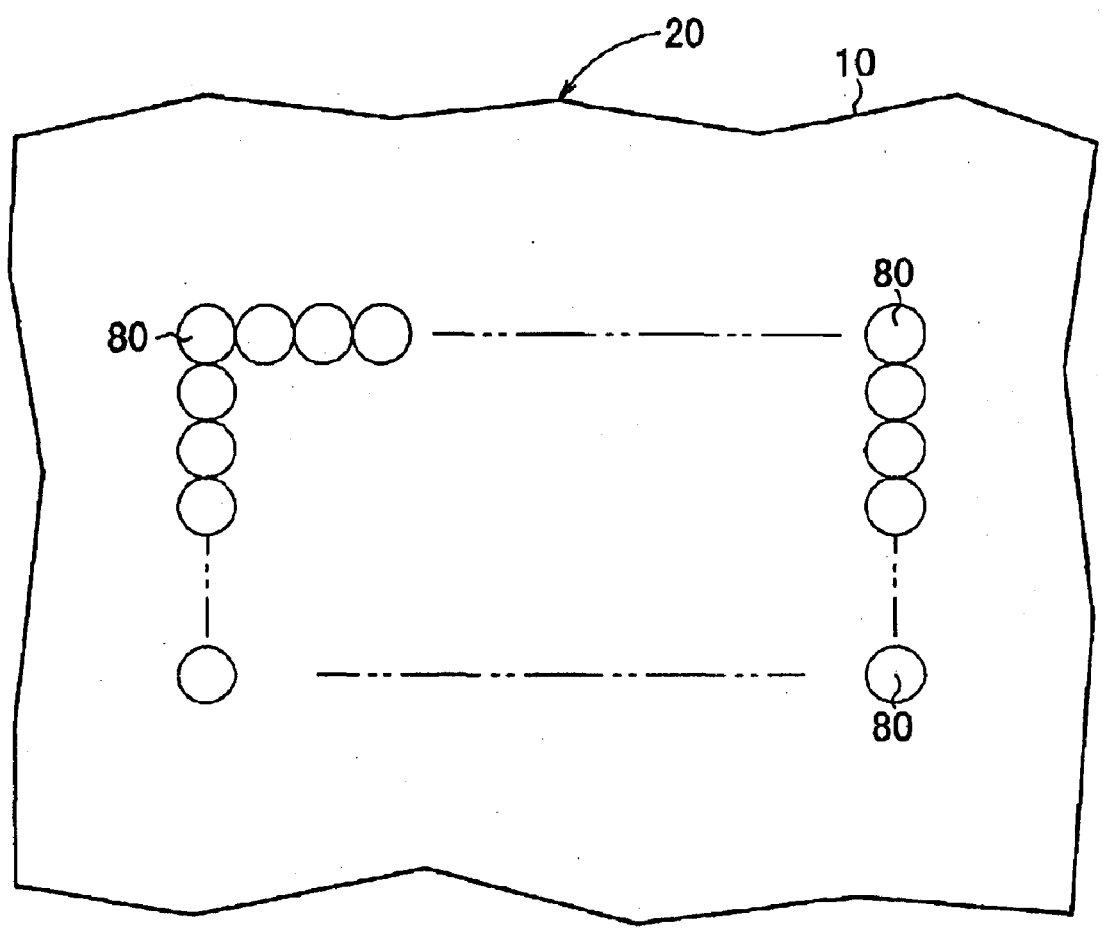
FIG. 12 illustrates a state in which spots are arranged in a matrix form.
Figure 13:
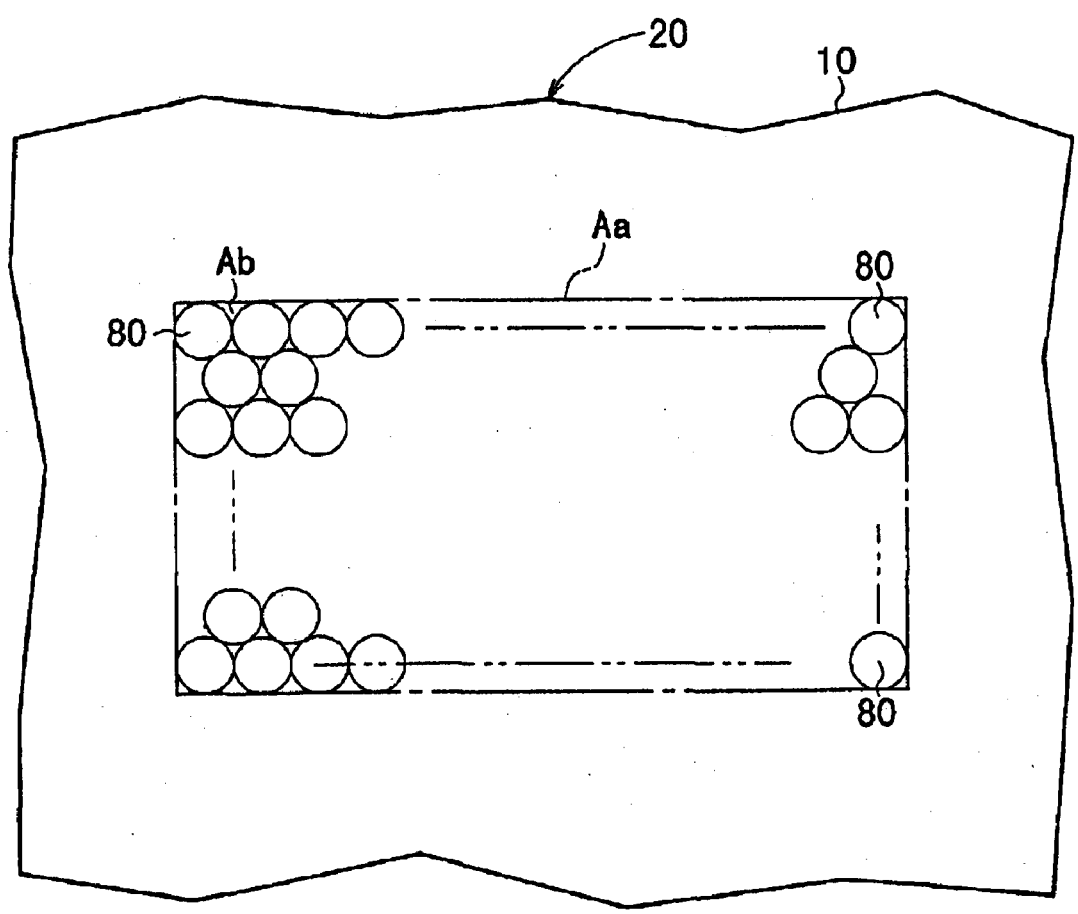
FIG. 13 illustrates a state in which spots are arranged in a zigzag form.

In the embodiment of the present invention, as shown in FIG. 12, when a large number of spots 80 are arranged, the spots 80 can be concentrated up to positions at which the adjoining spots 80 make contact with each other. Further, as shown in FIG. 13, a large number of spots 80 can be also arranged in a zigzag configuration. In this case, when the spots 80 are concentrated up to positions at which the adjoining spots 80 make contact with each other, the ratio of the non-deposition area Ab of the spots 80 (area Ab of the portion at which the spots 80 are not formed) with respect to the inspection effective area Aa (area Aa of the substantially rectangular region in which the spots 80 are arranged) on the base plate 10 is not more than about 9%.

As described above, in the embodiment of the present invention, it is possible to achieve the high concentration of the spots 80. Therefore, it is possible to perform the detailed genetic analysis for a large amount of the sample at once.

Figure 14A:
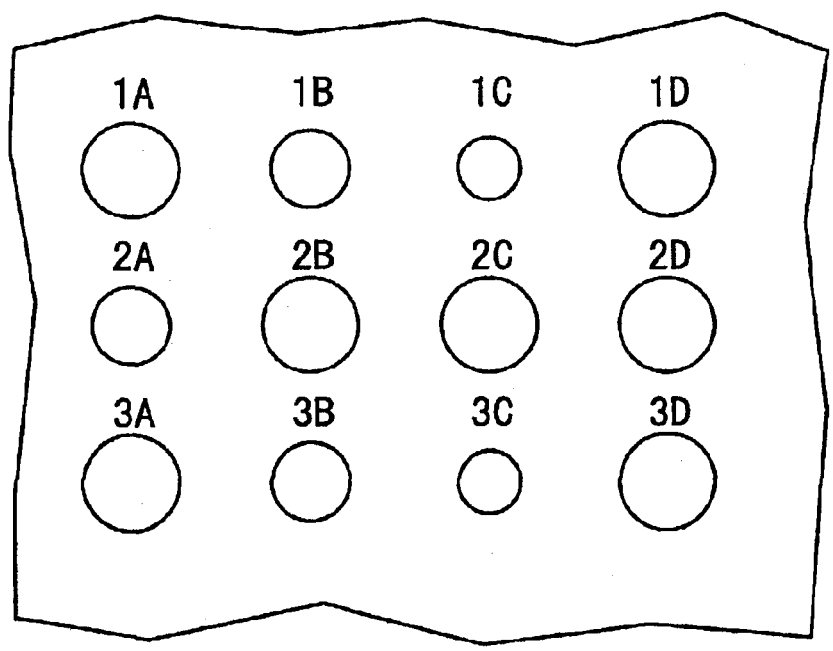
FIG. 14A illustrates a state in which a plurality of spots having different spot sizes are formed on a base plate.

In the embodiment of the present invention, as shown in FIG. 14A, a plurality of spots having different spot sizes can be formed on the base plate. In the example shown in FIG. 14A, when different amounts of DNA are immobilized on the spots, or when different species of DNA having different efficiencies of hybridization with a specimen are immobilized for the respective spots 1A to 3D with different types of DNA fragments, then the size of the spot, i.e., the diameter of the circular configuration in general is changed.

Specifically, the spots are formed as follows. That is, the spot diameter is large for each of the spots 1A, 1D, 2B, 2C, 2D, 3A, 3D in which the amount of DNA immobilized on the spot is small, or in which the DNA species having a low efficiency of hybridization with the specimen is immobilized. The spot diameter is intermediate for each of the intermediate spots 1B, 2A, 3B. The spot diameter is small for each of the spots 1C, 3C in which the amount of DNA immobilized on the spot is large, or in which the DNA species having a high efficiency of hybridization with the specimen is immobilized. Therefore, it is possible to suppress the dispersion of the ability to capture the specimen. Further, it is possible to suppress the deterioration of the quantitative performance and the dispersion of the inspection result which would be otherwise caused by the difference in detection sensitivity between the spots.

Figure 14B:
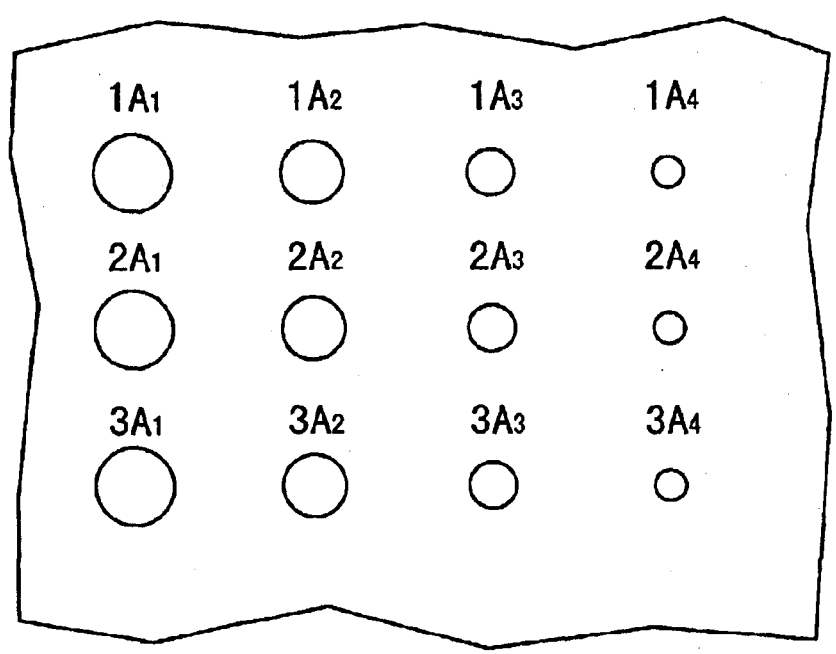
FIG. 14B illustrates a state in which four spots having different sizes respectively are formed for an identical DNA fragment.

In the embodiment of the present invention, as shown in FIG. 14B, a plurality of spots having different sizes (spot diameters) respectively can be formed for an identical. DNA fragment. The example shown in FIG. 14B is illustrative of a state in which four spots $A_1$ to $A_4$ having different sizes (spot diameters) respectively are formed for identical DNA fragments 1A, 2A, 3A. In this case, it is possible to recognize the degree of the reaction depending on the size of the spot, in addition to a digital inspection result to indicate whether or not the reaction occurs, with the spots of the corresponding DNA fragment. It is possible to obtain an analog inspection result for the specimen.

Figure 15A:
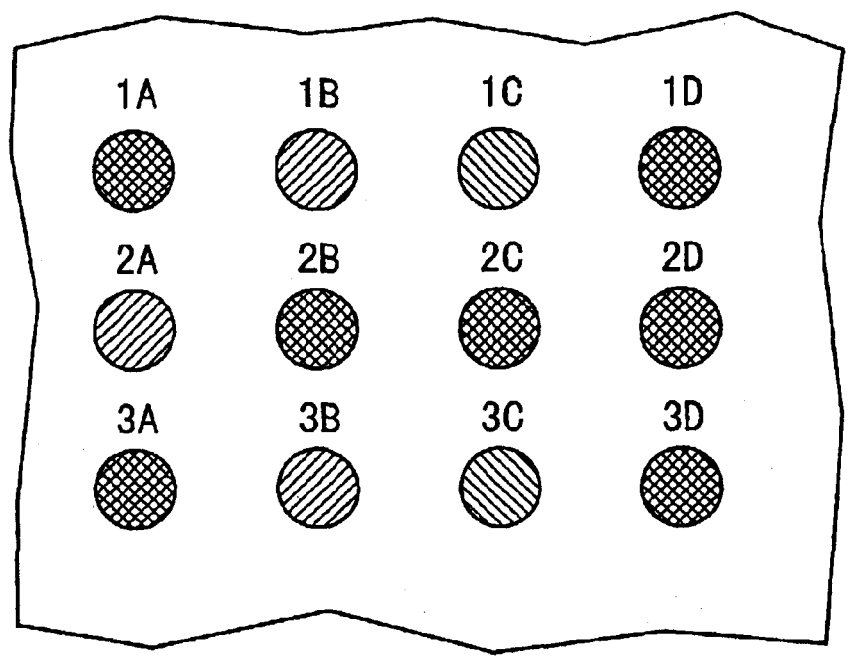
FIG. 15A illustrates a state in which a plurality of spots are formed, in which the amount of the capture per unit area immobilized in each of the spots differs.

In the embodiment of the present invention, as shown in FIG. 15A, it is possible to form a plurality of spots having different amounts per unit area of amounts of a DNA fragment immobilized in the respective spots. In the example shown in FIG. 15A, when different species of DNA having different efficiencies of hybridization with a specimen are immobilized for the respective spots 1A to 3D with different types of DNA fragments, the amount per unit area of the amount of the DNA fragment immobilized in each of the spots is changed.

Specifically, the spots are formed as follows. That is, the amount per unit area of the amount of the immobilized DNA fragment is large for each of the spots 1A, 1D, 2B, 2C, 2D, 3A, 3D in which the DNA species having a low efficiency of hybridization with the specimen is immobilized. The amount per unit area of the amount of the immobilized DNA fragment is intermediate for each of the intermediate spots 1B, 2A, 3B. The amount per unit area of the amount of the immobilized DNA fragment is small for each of the spots 1C, 3C in which the DNA species having a high efficiency of hybridization with the specimen is immobilized. Therefore, it is possible to suppress the dispersion of the ability to capture the specimen. Further, it is possible to suppress the deterioration of the quantitative performance and the dispersion of the inspection result which would be otherwise caused by the difference in detection sensitivity between the spots.

Figure 15B:
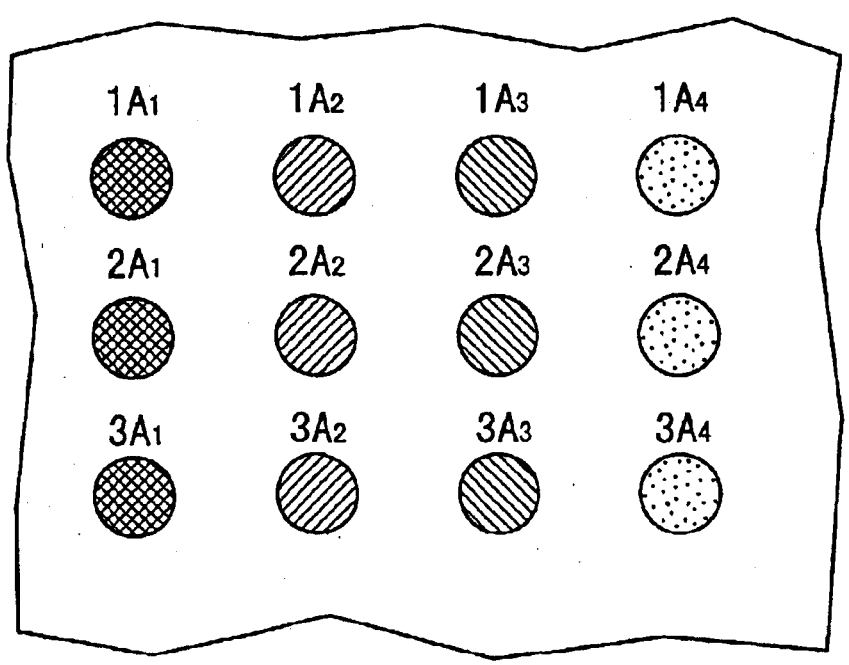
FIG. 15B illustrates a state in which four spots are formed for an identical DNA fragment, in which the amount of the immobilized capture per unit area differs respectively.

In the embodiment of the present invention, as shown in FIG. 15B, it is possible for an identical DNA fragment to form a plurality of spots having different amounts per unit area of amounts of the DNA fragment immobilized on the base plate respectively. The example shown in FIG. 15B is illustrative of a state in which four spots $A_1$ to $A_4$ having different amounts per unit area of amounts of DNA fragments immobilized on the base plate respectively are formed for the identical DNA fragments 1A, 2A, 3A. In this case, it is possible to recognize the degree of the reaction depending on the amount of the DNA fragment per unit area, in addition to a digital inspection result to indicate whether or not the reaction occurs, with the spots of the corresponding DNA fragment. It is possible to obtain an analog inspection result for the specimen.

Figure 17:
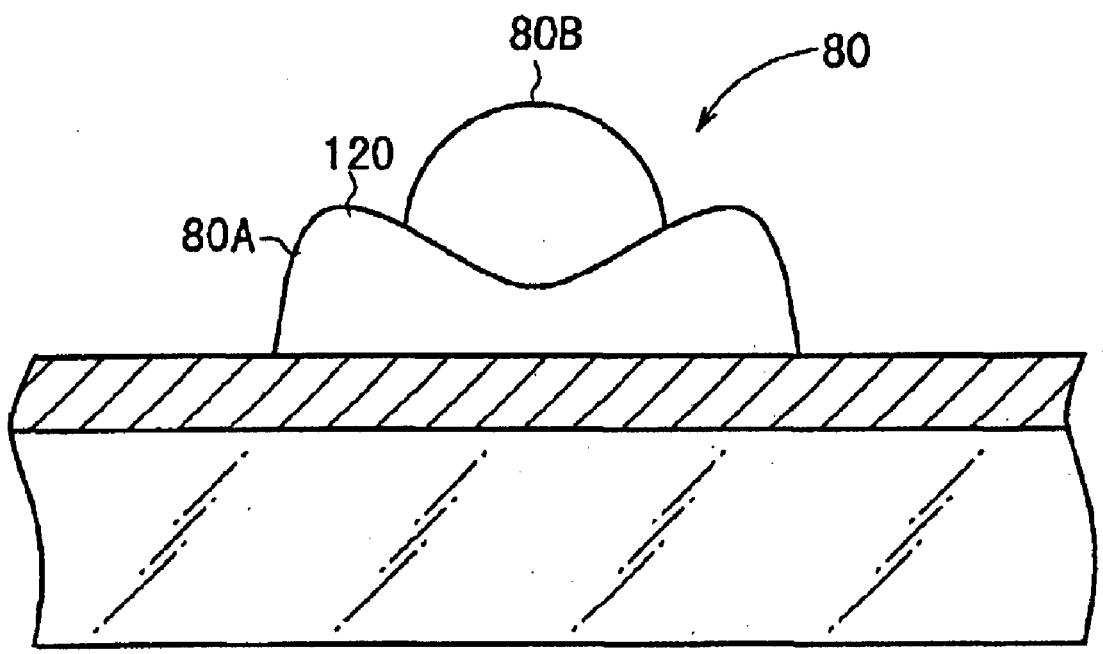
FIG. 17 shows a sectional view taken along a line XVII—XVII shown in FIG. 16.
Figure 18:
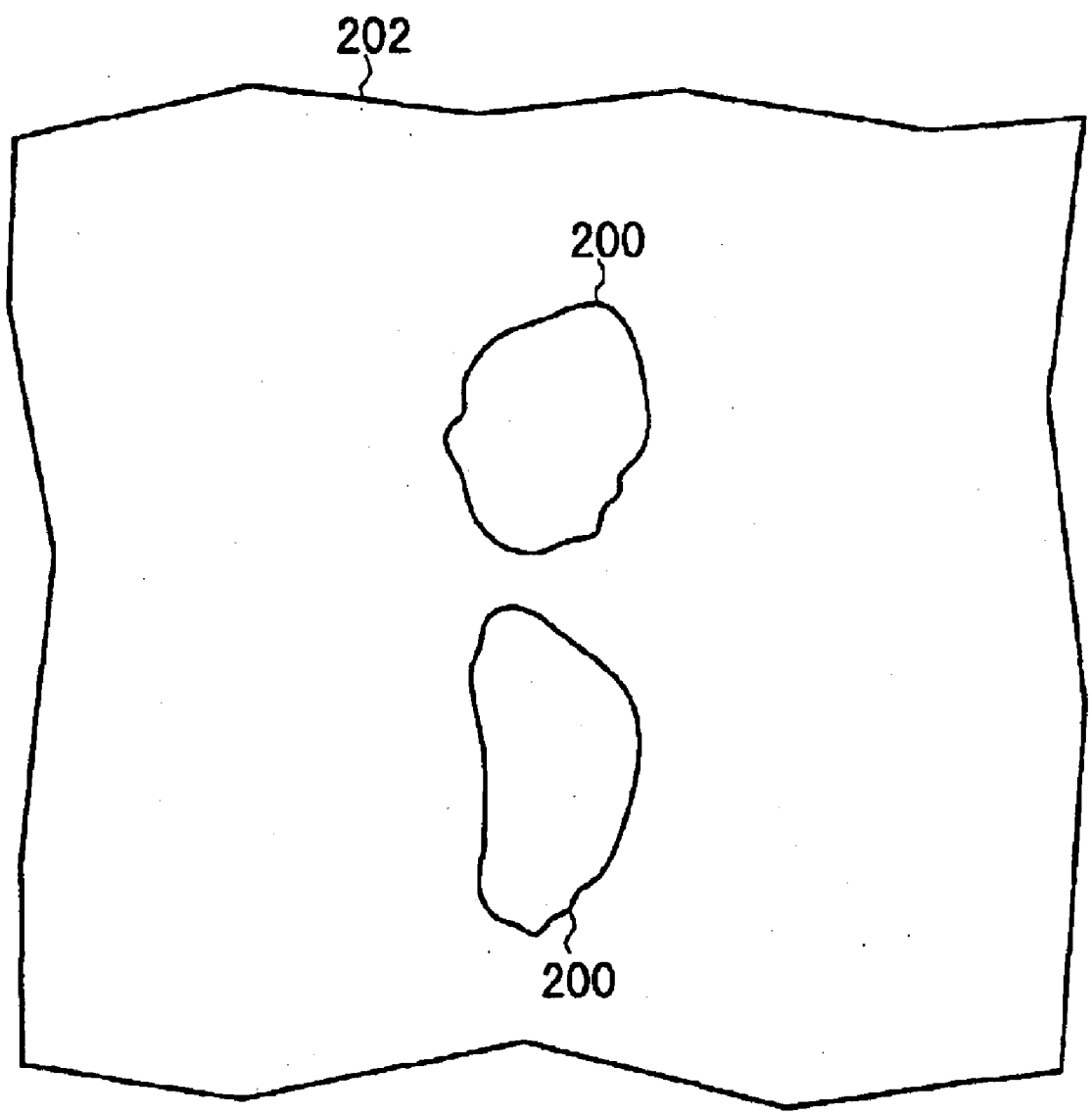
FIG. 18 illustrates shapes of conventional spots.

In the embodiment of the present invention, as shown in FIGS. 16 and 17, for example, a first layer spot 80A, which is formed on the base plate 10, has a so-called doughnut-shaped configuration in which a peripheral portion 120 (see FIG. 17) is ridged, for example, by adjusting the discharge power or the like of the micropipette 34. Further, after the spot 80A having the doughnut-shaped configuration is dried, a spot 80B, which contains a different DNA fragment and which has a substantially circular planar configuration, is formed on the spot 80A. Accordingly, the spots 80A, 80B, which contain the different samples respectively, can be formed at an identical spot formation position. In this case, it is possible to greatly reduce the arrangement area for the spot 80. It is possible to miniaturize the DNA microarray 20 itself.

When the spots composed of different types of samples are formed at the identical spot formation position, there is no limitation to the arrangement in which the formation position is allotted to the peripheral portion and the central portion of the spot as described above. However, when the effective spot areas are arranged concentrically as described above, an effect is obtained to reduce the dispersion of the shape between the different spots.

The DNA microarray as described above is preferably produced in accordance with an ink-jet method. Especially, when different samples are formed in an identical spot, or when spots of different samples are arranged in a contact manner, the production cannot be performed in accordance with the conventional pin system, because of the problem of pin contamination. However, the arrangement as described above can be efficiently realized with good accuracy by means of the ink-jet method in which spots are formed in a non-contact manner.

It is a matter of course that the DNA microarray according to the present invention is not limited to the embodiments described above, which may be embodied in other various forms without deviating from the gist of the present invention.

INDUSTRIAL APPLICABILITY

As explained above, the following effects can be obtained in accordance with the DNA microarray of the present invention.

(1) The inspection accuracy for the genetic analysis is improved, making it possible to perform the quantitative evaluation.

(2) It is possible to achieve the high concentration of spots, and it is possible to perform the detailed genetic analysis for a large amount of sample at once.

(3) It is possible to recognize the degree of the reaction depending on the amount of the immobilized DNA fragment, in addition to the digital inspection result to indicate whether or not the reaction occurs. Thus, it is possible to obtain the analog inspection result for a specimen.

What is claimed is:

1. A biochip comprising a large number of spots containing DNA arranged on a base plate, obtained by supplying, onto said base plate by means of an ink jet system, a plurality of types of capture solutions containing said DNA each of which is adapted to specifically react with a specimen and provide information about a structure within the specimen, wherein:

a plurality of said spots, which have different spot sizes, are formed on said base plate, wherein all of said spots have uniform detection sensitivity.

2. A biochip according to claim 1, wherein said plurality of spots are formed from the same capture solution.

3. A biochip according to claim 2, wherein said spots containing said DNA are formed by a method using an ink-jet system, in which said capture solution is impacted onto said base plate after being discharged into the atmosphere, and wherein a force of the discharge is controlled electrically.

4. A biochip according to claim 2, wherein said spots containing said DNA are formed by a method using an ink-jet system, in which said capture solution is impacted onto said base plate after being discharged into the atmosphere, and wherein the number of times of discharge at each spot and a force of the discharge are electrically controlled, respectively.

5. A biochip according to claim 1, wherein said spots containing said DNA are formed by a method using an ink-jet system, in which said capture solution is impacted onto said base plate after being discharged into the atmosphere, and wherein a force of the discharge is controlled electrically.

6. A biochip according to claim 1, wherein said spots containing said DNA are formed by a method using an ink-jet system, in which said capture solution is impacted onto said base plate after being discharged into the atmosphere, and wherein the number of times of discharge at each spot and a force of the discharge are electrically controlled, respectively.

7. A biochip comprising a large number of spots of DNA containing a capture material therein arranged on a base plate, obtained by supplying, onto said base plate by means of an ink jet system, a plurality of types of capture solutions containing said DNA each of which is adapted to specifically react with a specimen and provide information about a structure within the specimen, wherein:

a plurality of said spots are formed in which the concentration of the capture material in the capture solution varies from spot to spot, wherein all of said spots have uniform detection sensitivity.

8. A biochip according to claim 7, wherein said plurality of spots are formed from the same capture solution.

9. A biochip according to claim 8, wherein said spots containing said DNA are formed by a method using an ink-jet system, in which said capture solution is impacted onto said base plate after being discharged into the atmosphere, and wherein a force of the discharge is controlled electrically.

10. A biochip according to claim 8, wherein said spots containing said DNA are formed by a method using an ink-jet system, in which said capture solution is impacted onto said base plate after being discharged into the atmosphere, and wherein the number of times of discharge at each spot and a force of the discharge are electrically controlled, respectively.

11. A biochip according to claim 7, wherein said spots containing said DNA are formed by a method using an inkjet system, in which said capture solution is impacted onto said base plate after being discharged into the atmosphere, and wherein a force of the discharge is controlled electrically.

12. A biochip according to claim 7, wherein said spots containing said DNA are formed by a method using an ink-jet system, in which said capture solution is impacted onto said base plate after being discharged into the atmosphere, and wherein the number of times of discharge at each spot and a force of the discharge are electrically controlled, respectively.

13. A biochip comprising a large number of spots of containing DNA therein arranged on a base plate, obtained by supplying, onto said base plate by means of an ink jet system, a plurality of types of capture solutions containing said DNA each of which is adapted to specifically react with a specimen and provide information about a structure within the specimen, wherein:

a plurality of said spots are formed in which the concentration of said DNA in the capture solutions varies from spot to spot, wherein all of said spots have uniform detection sensitivity and said base plate comprises glass.

* * * * *

UNITED STATES PATENT AND TRADEMARK OFFICE
CERTIFICATE OF CORRECTION

PATENT NO. : 6,753,144 B2
DATED : June 22, 2004
INVENTOR(S) : Toshikazu Hirota and Takao Ohnishi It is certified that error appears in the above-identified patent and that said Letters Patent is hereby corrected as shown below:

Column 7,
Line 22, replace "$\mu$g/ml." with -- $\mu$g/$\mu$liter. --

Column 18,
Line 32, delete the second occurrence of "of"

Signed and Sealed this

Thirtieth Day of November, 2004

JON W. DUDAS
*Director of the United States Patent and Trademark Office*